(12) United States Patent
Bernhardt et al.

(10) Patent No.: US 7,879,790 B2
(45) Date of Patent: *Feb. 1, 2011

(54) MIXED SALTS OF SULFONATED ESTOLIDES AND OTHER DERIVATIVES OF FATTY ACIDS, AND METHODS OF MAKING THEM

(75) Inventors: Randal J. Bernhardt, Antioch, IL (US); Gregory P. Dado, Chicago, IL (US); Eddie I. Filipovic, Evanston, IL (US); Jeremy Aaron Weitgenant, Grayslake, IL (US)

(73) Assignee: Stepan Company, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/506,861

(22) Filed: Jul. 21, 2009

(65) Prior Publication Data

US 2010/0022429 A1    Jan. 28, 2010

Related U.S. Application Data

(63) Continuation-in-part of application No. 12/353,751, filed on Jan. 14, 2009, now Pat. No. 7,666,828.

(60) Provisional application No. 61/022,662, filed on Jan. 22, 2008.

(51) Int. Cl.
*C11D 1/28* (2006.01)
(52) U.S. Cl. .......................... 510/495; 554/96
(58) Field of Classification Search ................. 510/495; 554/96
See application file for complete search history.

(56) References Cited

U.S. PATENT DOCUMENTS

| | | | |
|---|---|---|---|
| 2,581,375 A | 1/1952 | De Groote et al. |
| 2,743,288 A | 4/1956 | Rueggeberg et al. |
| 2,995,524 A | 8/1961 | Wylie et al. |
| 3,332,880 A | 7/1967 | Kessler et al. |
| 3,377,290 A | 4/1968 | Werner et al. |
| 3,664,961 A | 5/1972 | Norris |
| 3,668,153 A | 6/1972 | Crotty |
| 3,898,187 A | 8/1975 | Miller |
| 3,929,678 A | 12/1975 | Laughlin et al. |
| 4,228,044 A | 10/1980 | Cambre |
| 4,435,307 A | 3/1984 | Barbesgaard et al. |
| 4,438,025 A | 3/1984 | Satsuki et al. |
| 4,507,219 A | 3/1985 | Hughes |
| 4,548,744 A | 10/1985 | Connor |
| 4,561,998 A | 12/1985 | Wertz et al. |
| 4,597,898 A | 7/1986 | Vander Meer |
| 4,663,071 A | 5/1987 | Bush et al. |
| 4,816,188 A | 3/1989 | Kitano et al. |
| 4,936,551 A | 6/1990 | Behler et al. |
| 5,002,683 A | 3/1991 | Behler et al. |
| 5,071,594 A | 12/1991 | Borland et al. |
| 5,075,501 A | 12/1991 | Borland et al. |
| 5,294,726 A | 3/1994 | Behler et al. |
| 5,329,030 A | 7/1994 | Schenker et al. |
| 5,429,684 A | 7/1995 | Osberghaus et al. |
| 5,441,156 A | 8/1995 | Fabry et al. |
| 5,466,394 A | 11/1995 | de Buzzaccarini et al. |
| 5,576,282 A | 11/1996 | Miracle et al. |
| 5,622,925 A | 4/1997 | de Buzzaccarini et al. |
| 5,679,630 A | 10/1997 | Baeck et al. |
| 5,776,872 A | 7/1998 | Giret et al. |
| 5,883,062 A | 3/1999 | Addison et al. |
| 5,906,973 A | 5/1999 | Ouzounis et al. |
| 5,929,022 A | 7/1999 | Velazquez |
| 6,017,871 A | 1/2000 | Baeck et al. |
| 6,018,063 A | 1/2000 | Isbell |
| 6,048,836 A | 4/2000 | Romano et al. |
| 6,172,026 B1 | 1/2001 | Ospinal |
| 6,242,406 B1 | 6/2001 | Katsuda et al. |
| 6,294,513 B1 | 9/2001 | Jensen et al. |
| 6,306,812 B1 | 10/2001 | Perkins et al. |
| 6,326,348 B1 | 12/2001 | Vinson et al. |
| 6,605,579 B1 | 8/2003 | Arvanitidou et al. |
| 6,627,592 B1 | 9/2003 | Shamayeli |

(Continued)

FOREIGN PATENT DOCUMENTS

DE    2247832    4/1973

(Continued)

OTHER PUBLICATIONS

A.J. Stirton, et al.: "Surface-active properties of salts of alpha-sulphonated acids and esters" Journal Of The American Oil Chemists' Society, vol. 13, No. 1, Jan. 1954, pp. 13-16, XP002537683 Springer, Berlin, DE ISSN: 0003-021X DOI: 10.1007/BF02544763 The Whole Document.

(Continued)

*Primary Examiner*—John R Hardee
(74) *Attorney, Agent, or Firm*—McAndrews, Held & Malloy, Ltd.

(57) ABSTRACT

Sulfo-estolides and methods of making them are described. Also described are phase-stable compositions formed from mixtures of different salts of sulfo-estolides, particularly mixtures of sodium and potassium salts of sulfo-estolides, and methods of obtaining phase-stable sulfo-estolide mixed salt compositions. The sulfo-estolide mixed salt compositions can be used in detergent formulations, such as laundry detergents, household, industrial and institutional cleaning formulations, and person care products.

34 Claims, No Drawings

U.S. PATENT DOCUMENTS

| | | | |
|---|---|---|---|
| 6,797,011 | B2 | 9/2004 | Blangiforti |
| 6,878,695 | B2 | 4/2005 | Woo et al. |
| 6,903,064 | B1 | 6/2005 | Kasturi et al. |
| 6,949,498 | B2 | 9/2005 | Murphy et al. |
| 6,953,849 | B2 | 10/2005 | Vali |
| 7,326,675 | B2 | 2/2008 | Schneiderman et al. |
| 7,666,828 | B2 * | 2/2010 | Bernhardt et al. ............ 510/495 |
| 2002/0039979 | A1 | 4/2002 | Aszman et al. |
| 2002/0187909 | A1 | 12/2002 | Gupta et al. |
| 2004/0071653 | A1 | 4/2004 | Bratescu et al. |
| 2004/0242920 | A1 | 12/2004 | Dado et al. |
| 2005/0215456 | A1 | 9/2005 | Goo et al. |
| 2007/0128129 | A1 | 6/2007 | Stehr |
| 2007/0202069 | A1 | 8/2007 | Tamareselvy |
| 2008/0015135 | A1 | 1/2008 | Debuzzaccarini |
| 2009/0054294 | A1 | 2/2009 | Theiler |

FOREIGN PATENT DOCUMENTS

| | | |
|---|---|---|
| DE | 3926345 A1 | 2/1991 |
| EP | 0070077 | 1/1983 |
| EP | 0075996 | 4/1983 |
| EP | 0094118 | 11/1983 |
| EP | 111965 | 6/1984 |
| EP | 111984 | 6/1984 |
| EP | 112592 | 7/1984 |
| EP | 0485500 A1 | 5/1992 |
| EP | 0 511 091 A1 | 10/1992 |
| GB | 1 047 772 A | 11/1966 |
| GB | 1082179 | 9/1967 |
| GB | 1278421 A1 | 6/1972 |
| GB | 1372034 | 10/1974 |
| GB | 1 380 390 A | 1/1975 |
| GB | 1380390 A | 1/1975 |
| GB | 2075028 | 11/1981 |
| GB | 2095275 | 9/1982 |
| GB | 2247832 | 3/1992 |
| WO | 88/09367 | 12/1988 |
| WO | 89/09813 | 10/1989 |
| WO | WO 90/02116 A1 | 3/1990 |
| WO | WO 91/02045 A1 | 2/1991 |
| WO | WO 91/13961 A1 | 9/1991 |
| WO | 92/05249 | 4/1992 |
| WO | WO 92/15660 A1 | 9/1992 |
| WO | 99/05242 | 2/1999 |
| WO | 00/18363 A1 | 4/2000 |
| WO | WO0018363 A1 | 4/2000 |
| WO | 00/58430 A1 | 10/2000 |
| WO | 01/53247 A1 | 7/2001 |
| WO | WO0153247 A1 | 7/2001 |
| WO | 2005/113735 A1 | 12/2005 |
| WO | 2006/062665 | 6/2006 |
| WO | WO 2006/062665 * | 6/2006 |
| WO | 2008/137769 | 11/2008 |
| WO | 2009/094336 | 7/2009 |
| WO | WO 2009/094336 * | 7/2009 |
| WO | WO2009094336 A2 | 7/2009 |

OTHER PUBLICATIONS

PCT International Search Report and Written Opinion from International Application No. PCT/US2009/031455 mailed on Aug. 17, 2009.

PCT International Search Report and Written Opinion from International Application No. PCT/US2009/031608 mailed on Oct. 29, 2009.

PCT International Search Report and Written Opinion from International Application No. PCT/US2009/051299 mailed on Oct. 20, 2009.

PCT International Search Report and Written Opinion from International Application No. PCT/US2009/051318 mailed on Oct. 22, 2009.

PCT International Search Report and Written Opinion from International Application No. PCT/US2009/051319 mailed on Oct. 20, 2009.

PCT International Search Report and Written Opinion from International Application No. PCT/US2009/051464 mailed on Oct. 22, 2009.

"Surface Active Agents and Detergents" (vol. I and II by Schwartz, Perry and Berch).

Surfactant Science Series, Marcel Dekker, vol. 25 and 48.

Foams Fundamentals and Applications in the Petrochemical Industry, edited by Laurier L. Schraman (1994).

Handbook of Water-Soluble Gums and Resins, Glossary and Chapters 3, 4, 12 and 13, Robert L. Davidson, McGraw-Hill Book Co., New York, NY (1980).

Stein et al., J. Amer. Oil Chemists Soc., 52:323-329 (1975).

Knaggs et al., J. Amer. Oil Chemists Soc., 42(9):805-810 (1965).

Kato et al., J. Surfactants and Detergents, 6(4):331-337 (2003).

Kirk-Othmer, Encyclopedia of Chemical Technology, 5th ed., vol. 23, Wiley-Interscience, Hoboken, NJ (2007), "Sulfonation and Sulfation", pp. 513-562.

McCutcheons' 2009 Functional Materials of North American Edition, vol. 2, pp. 239-246 (2009).

Neiditch et al., J. Amer. Oil Chemists Soc., 57(12):426-429 (1980).

Office Action in U.S. Appl. No. 12/353,751, dated Dec. 1, 2009.

Office Action in U.S. Appl. No. 12/353,751, dated Nov. 17, 2009.

Office Action in U.S. Appl. No. 12/506,977, dated Apr. 16, 2010.

Steinberg, Preservatives for Cosmetics Manual, 2nd Ed., by David S. Steinbens (2006).

Sauls et al., J. Amer. Oil Chemists Soc., 33(9):383-389 (1956).

SDA "Washers and Detergents" publication 2005; http://www.cleaning101.com/laundry/HE.pdf.

Surfactants and Interfacial Phenomena, 3rd ed., by Milton Rosen, published by John Wiley & Sons, Inc., Hoboken, NJ (2004).

Surfactant Science Series, Marcel Dekker, vols. 25 and 48.

Stirton et al., J. Amer. Oil Chemists Soc., 13(1):13-16 (1954).

Notification of Transmittal of the International Search Report and Written Opinion of the International Search Authority, in PCT/US2009/051294, dated Mar. 25, 2010.

Stirton et al., "Surface-Active Properties of Salts of Alpha-Sulphonated Acids and Esters", Journal of the American Oil Chemists' Society, vol. 13, No. 1, Jan. 1, 1954, pp. 13-16, XP002537683, Springer, Berlin, DE, ISSN 0003-021X.

European Search Report in EP 09009490.5, dated May 17, 2010.

International Search Report and Written Opinion in PCT/US09/51312, dated Mar. 24, 2010.

International Search Report and Written Opinion in PCT/US10/29654, dated May 25, 2010.

* cited by examiner

MIXED SALTS OF SULFONATED ESTOLIDES AND OTHER DERIVATIVES OF FATTY ACIDS, AND METHODS OF MAKING THEM

RELATED APPLICATIONS

This application is a continuation-in-part application of U.S. application Ser. No. 12/353,751 entitled "Sulfonated Estolides and Other Derivatives of Fatty Acids, Methods of Making Them, and Compositions and Processes Employing Them" filed on Jan. 14, 2009, which claims priority to U.S. Provisional Application Ser. No. 61/022,662, filed on Jan. 22, 2008.

BACKGROUND OF THE INVENTION

The present technology, in general, relates to sulfo-estolides. More particularly, the present technology relates to phase-stable compositions comprising mixed salts of sulfo-estolides, and methods of making phase-stable sulfo-estolide compositions comprising mixed salts of sulfo-estolides.

BRIEF SUMMARY OF THE INVENTION

In at least one aspect, the present technology provides a composition comprising a mixture of sodium and potassium salts of sulfo-estolides, which have the following Formula:

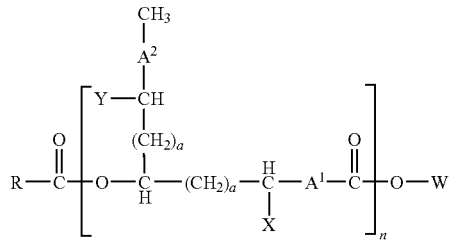

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from 1 to 24; W is a sodium or potassium cation, H, or an alkyl or substituted alkyl group; and Z is a sodium or potassium cation; wherein the sodium and potassium salts are present in the mixture in amounts sufficient to obtain a composition that is a clear, homogeneous liquid product.

In another aspect, the present technology provides a process for preparing a phase-stable sulfo-estolide composition comprising the steps of: providing at least one sulfonated intermediate made by sulfonating at least one unsaturated fatty carboxylic acid having 8 to 24 carbon atoms; reacting the sulfonated intermediate with a chain termination agent having 4 to 24 carbon atoms to form at least one sulfo-estolide; neutralizing the at least one sulfo-estolide by adding to the at least one sulfo-estolide a caustic agent selected from the group consisting of KOH, NaOH and mixtures thereof to obtain a neutralized sulfo-estolide salt; bleaching the neutralized sulfo-estolide salt with hydrogen peroxide at a pH level in the range of about 4.5 to about 7.5; and adding additional KOH, NaOH or mixtures thereof before, during or after the bleaching step in an amount sufficient to obtain a mixture of potassium and sodium sulfo-estolide salts that results in a phase-stable sulfo-estolide composition that is clear and homogeneous.

Another aspect of the present technology provides a laundry detergent composition, comprising: about 2% to about 90% by weight of a mixture of sodium and potassium salts of sulfo-estolides having the following Formula 1:

Formula 1

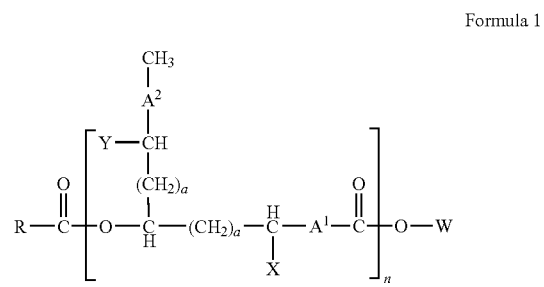

wherein n is an integer from 1-30; one of X and Y is SO3-Z, the other of X and Y is H, and X and Y are independently assigned in each repeating unit; A1 and A2 are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to 24 carbon atoms; W is a sodium or potassium cation, H, or an alkyl or substituted alkyl group; Z is a sodium or potassium cation; about 2% to about 40% by weight of at least one nonionic surfactant; 0% to about 35% by weight of at least one alcohol ether sulfate; 0% to about 6% by weight of lauryl dimethlyamine oxide; 0% to about 10% by weight of oleamide diethanolamine; 0% to about 6% by weight of $C_{12}EO_3$; 0% to about 10% by weight of coconut fatty acid; 0% to about 3% by weight of borax pentahydrate; 0% to about 6% by weight of propylene glycol; 0% to about 10% by weight of sodium citrate; 0% to about 6% by weight of triethanolamine; 0% to about 6% by weight of monoethanolamine; 0% to about 1% by weight of at least one fluorescent whitening agent; 0% to about 1.5% by weight of at least one anti-redeposition agent; 0% to about 2% by weight of at least one thickener; 0% to about 20% by weight of at least one thinner; 0% to about 2% by weight of at least one protease; 0% to about 2% by weight of at least one amylase; and 0% to about 2% by weight of at least one cellulase.

Moreover, another aspect of the present technology provides a laundry detergent composition, comprising: about 2% to about 90% by weight of a mixture of sodium and potassium salts of sulfo-estolides having the following Formula 1:

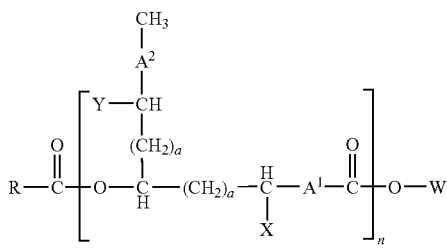

wherein n is an integer from 1-30; one of X and Y is SO3-Z, the other of X and Y is H, and X and Y are independently assigned in each repeating unit; A1 and A2 are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to 24 carbon atoms; W is a sodium or potassium cation, H, or an alkyl or substituted alkyl group; Z is a sodium or potassium cation; about 2% to about 40% by weight of at least one nonionic surfactant; 0% to about 35% by weight of at least one or more alcohol ether sulfate; 0% to about 6% by weight of lauryl dimethylamine oxide; 0% to about 13% by weight of $C_{12}EO_3$; 0% to about 10% by weight of coconut fatty acid; 0% to about 10% by weight of sodium metasilicate; 0% to about 10% by weight of sodium carbonate; 0% to about 1% by weight of at least one fluorescent whitening agent; 0% to about 1.5% by weight of at least one anti-redeposition agent; 0% to about 2% by weight of at least one thickener; and 0% to about 20% by weight of at least one thinner.

Another aspect of the present technology provides a composition comprising a mixture of salts of sulfo-estolides, which have the following Formula:

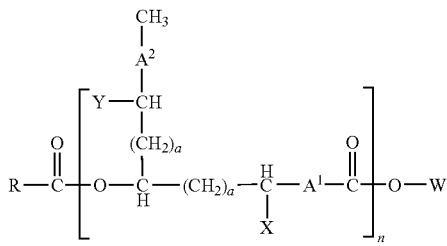

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from 1 to 24; W is a cation, H, or an alkyl or substituted alkyl group; and Z is a cation; wherein the salts are present in the mixture in amounts sufficient to obtain a composition that is a clear, homogeneous liquid product.

DETAILED DESCRIPTION OF THE INVENTION

The present technology, in general, relates to sulfo-estolides. More particularly, the present technology relates to phase-stable compositions comprising mixed salts of sulfo-estolides, and methods of making compositions comprising mixtures of sulfo-estolide salts having improved phase stability, and incorporation of such compositions into a variety of formulations for laundry detergents, industrial cleaning and home cleaning, and personal care applications among others. The compositions of the present technology described herein include, but are not limited to, sulfo-estolides having the structure of Formula 1:

Formula 1

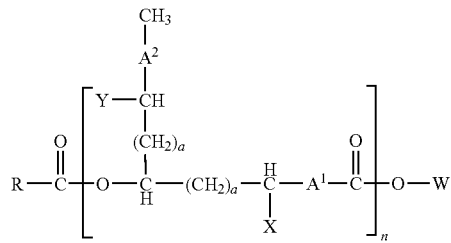

In Formula 1:
n is an integer from about 1 to about 30, alternatively about 1 to about 10, alternatively 1 to 4, alternatively 1, 2, or 3, alternatively 1 or 2, alternatively 1; or mixtures thereof,
One of X and Y is $SO_3^-Z$, the other of X and Y is H (i.e., a hydrogen atom), and X and Y are independently assigned in each repeating unit;
$A^1$ and $A^2$ are independently selected linear or branched, saturated or unsaturated, substituted or unsubstituted alkyl diradicals, wherein the total number of carbons for each repeating unit is independent and in the range of $C_8$ to $C_{22}$. As defined herein, the term "alkyl diradical" is meant to refer to a linking hydrocarbon or alkylene segment, for example but by no means limited to —$(CH_2)_3$—, —$(CH_2)_4$—, —$(CH_2)_5$—, and so forth;
a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively;
R can be linear or branched, saturated or unsaturated, substituted or un-substituted hydrocarbon, wherein the total number of carbon atoms can be from about 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 carbon atoms to about 21 carbon atoms, alternatively from about 8 carbon atoms to about 16 carbon atoms;
W is a monovalent or divalent metal; ammonium; substituted ammonium; H; or a linear or branched, substituted or unsubstituted alkyl having from about 1 carbon atom to about 22 carbon atoms. For example, W can be an alkali or alkaline earth metal cation, with potassium or sodium being preferred in certain embodiments. Alternatively, W can be a glycerine joined by an ester linkage, e.g., a substituted C3 alkyl such that the structure of Formula 1 is incorporated one or more times as an ester in a monoglyceride, a diglyceride, or a triglyceride.

Z is H or a monovalent or divalent metal cation, ammonium or substituted ammonium cation, preferably an alkali or alkaline earth metal cation, for example potassium, sodium, calcium, or magnesium, with potassium or sodium being preferred in certain embodiments.

The above structure is illustrative of the sulfo-estolide products that may be derived from, for example, linear unsaturated fatty acid feedstocks. It is understood that sultone hydrolyzed products and structures of a comparable nature may be derived from branched and/or substituted unsaturated fatty acids or mixtures of linear and branched and/or substituted unsaturated fatty acids.

Additional sulfo-estolide compositions may be produced from fatty acid feedstocks comprising polyunsaturated fatty acids, wherein $A^1$ and $A^2$ may be independently selected from the set of alkyl diradicals that are: a) saturated; b) unsaturated, c) unsaturated and substituted with a sulfonate group, d) substituted with a hydroxyl group and a sulfonate group; or e) substituted with a ester group and a sulfonate group (i.e., a sulfo-estolide).

In another embodiment of the present technology, the sulfo-estolide compositions are comprised of carboxylic esters, or are reported in an ester analysis as carboxylic esters. Although it is contemplated that at least some of these carboxylic esters are sulfo-estolides, the presently described technology is not limited by the accuracy of this belief, for example the compositions may contain carboxylic esters wherein X and Y within one or more repeating units, in Formula 1, are both H.

In another embodiment of the present technology, the sulfo-estolide compositions are comprised of a sulfo-estolide of Formula 1 and a non-sulfonated estolide which comprises two or more fatty acid chains that does not contain a sulfonate group.

DEFINITIONS

The term "sulfo-estolide" ("SE") is used herein to describe Formula 1. The term "partially hydrolyzed sulfo-estolide" ("PHSE") describes compositions of Formula 1 wherein the esters have been partially hydrolyzed between, for example, about 1% to about 95%. The term "hydrolyzed sulfo-estolide" ("HSE") describes compositions of Formula 1 wherein the esters have been fully hydrolyzed (e.g., greater than about 95%).

The term "sultone hydrolyzed product" ("SHP") is used herein to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10.

The resulting SHP contains carboxylic acid esters at a level that corresponds to about 5 to about 95 mol %, alternatively about 20 mol % to about 60 mol %, alternatively about 20 mol % to about 45 mol %, alternatively about 30 mol % to about 45 mol % of the total carboxylic functionality in the composition. It is contemplated that none or few of the esters (whether they are sulfo-estolides or not) are hydrolyzed in the process of making SHP. By processing at a low temperature and neutralizing the acid as it leaves the sulfonator as quickly as possible, it is contemplated that lower ester levels will be obtained. Although not wanting to be bound by any particular theory, it is believed that through improvements and/or enhancements of process conditions of the present technology for production of esters, it is contemplated that products that have higher ester content will be obtained. For example, it is further believed that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used herein to describe a sulfonate composition that is produced from unsaturated fatty acids by sulfonation with $SO_3$ to produce sulfo-estolide and subsequent hydrolysis of greater than about 95% of the carboxylic esters. For example the resulting product may have a carboxylic ester content that corresponds to less than about 5 mol %, alternatively less than about 2 mol %, alternatively less than about 1 mol % of the total carboxylic functionality in the composition.

The term "partially ester hydrolyzed products" ("PEHP") is used herein to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

As defined herein, the term "free alkalinity" is meant to refer to the total amount of carboxylate anion and hydroxide present in a composition, as may be measured by, for example, potentiometric titration of an aqueous solution with aqueous strong acid, for example HCl, to an endpoint of about pH 3 to about pH 4.5, or alternatively to bromophenol blue endpoint.

As defined herein, the term "free caustic" is meant to refer to the total amount of excess strong alkalinity present in a composition, as may be measured by, for example potentiometric titration of an aqueous solution with aqueous strong acid, for example HCl, to an endpoint of about pH 9 to about pH 11.

A "repeating unit" means one instance of the subject matter enclosed by brackets in a formula. For example, if n=15 for a given molecule according to Formula 1, the molecule has 15 instances of the bracketed structure. Each instance of the bracketed structure can be identical to or different from other instances of the bracketed structure. For example, the Y moiety in Formula 1 can be H in one repeating unit and —$SO_3^-Z$ in another repeating unit of the same molecule.

Making SE or Other Carboxylic Esters

A suitable starting material for the presently described process for preparing one or more compositions of the present technology is a fatty acid (fatty carboxylic acid). Fatty acids that may be suitable for use in the practice of the present technology include but are not limited to linear unsaturated fatty acids of about 8 carbon atoms to about 24 carbon atoms, branched unsaturated fatty acids of about 8 carbon atoms to about 24 carbon atoms, or mixtures thereof. Unsaturated fatty acids provided from commercial sources containing both saturated and unsaturated fatty acids are suitable for use in the practice of the present technology. Mixtures of saturated fatty acids and unsaturated fatty acids are also contemplated. In a non-limiting example, fatty acid mixtures that are rich in oleic acid (cis-9-octadecenoic acid) are suitable feedstocks. Other unsaturated fatty acids, including but not limited to, trans-octadecenoic acids or palmitoleic acid may also be employed in the presently described technology.

Suitable feedstocks may be derived from vegetable and/or animal sources, including but not limited to fatty acids and fatty acid mixtures derived from canola oil, corn oil, cottonseed oil, linseed oil, olive oil, palm oil, peanut oil, rapeseed oil, safflower oil, sesame oil, soybean oil, sunflower oil, tall oil, tung oil, lard, poultry fat, BFT (bleachable fancy tallow), edible tallow, coconut oil, cuphea oil, yellow grease and combinations of these. Also contemplated are genetically modified or engineered oils that include but are not limited to high oleic sunflower or soybean oil. In some embodiments, the preferred unsaturated fatty acid feedstocks may contain reduced levels of polyunsaturated fatty acids, for example, less than 15%, alternatively less than about 10%, alternatively less than about 5% on a total weight basis. In some additional embodiments, the fatty acid feedstocks may be obtained by the partial hydrogenation of unsaturated triglycerides, for example soybean oil, followed by hydrolysis of the oil to afford fatty acids that are enriched in monounsaturated fatty acids and depleted in polyunsaturated fatty acids. The above-noted triglycerides that can be optionally hydrogenated can also be used as feedstocks, alone or in combination with fatty acids. Still further, in some embodiments of the presently described technology, suitable feedstocks may include those that contain appreciable amounts of saturated fatty acids, for example up to about 80%, alternatively about 50%, alternatively about 30%, alternatively about 20% saturated fatty acid by weight. Alternatively, the feedstocks may be enriched in mono unsaturated fatty acids, for example, via distillation; however, undistilled feedstocks are preferred due to lower cost.

In certain embodiments, a chain termination agent can be included in the reaction to reduce or prevent the formulation of products of Formula 1 in which n is greater than one (1). The chain termination agent can be, for example, a saturated or unsaturated, substituted or unsubstituted, aliphatic or aromatic carboxylic acid having from about 7 carbon atoms to about 22 carbon atoms, or a combination of any two or more of these. The contemplated characteristic of a chain termination agent preferred for the present purpose is that it can form an ester. One class of preferred chain termination agents is a saturated fatty acid having from about 8 carbon atoms to about 22 carbon atoms, optionally from about 8 carbon atoms to about 14 carbon atoms, optionally about 8 carbon atoms, about 10 carbon atoms, or about 12 carbon atoms or mixtures of these fatty acid species.

The compounds of Formula 1 and related compounds (for example, where n=0) can be made, for example, by: a) $SO_3$ sulfonation of a fatty acid, for example oleic acid; b) neutralization with aqueous caustic to afford a sulfonate salt solution with a pH in the range of about 4 to about 10; or c) hydrolysis of the resulting sultones, maintaining the reaction mixture at a pH of about 4 to about 10, alternatively at a pH of about 8, alternatively at a pH of about 7. Sulfonation can be carried out, for example, using a falling film $SO_3$ process.

Alternatively, the compounds of Formula 1 and related compounds (for example, where Z=H and W=H) can be made, for example, by falling film $SO_3$ sulfonation of a fatty acid, for example oleic acid, where the process temperature of the sulfonation is sufficient, for example greater than about 20° C., to result in the formation of carboxylic esters.

Continuous $SO_3$ sulfonation processes, including those that utilize falling film reactors such as those described in Kirk-Othmer Encyclopedia of Chemical Technology, 5th ed., Vol. 23, Wiley-Interscience, Hoboken, N.J.: 2007, entry entitled "Sulfonation and Sulfation", pp. 513-562, which is hereby incorporated by reference, are suitable for conducting the sulfonation of feedstocks comprising unsaturated fatty acids in accordance with the practice of the presently described technology. For example, a monotube concentric reactor, annular film reactor, or multitube film reactor can be used to contact an unsaturated fatty acid feedstock, for example oleic acid, with a gaseous stream of $SO_3$ that is diluted with dry air. The molar ratio of $SO_3$ to alkene functionality in the fatty acid feedstock may be from about 0.3 to about 1.3, alternatively from about 0.5 to about 1.2, alternatively from about 0.8 to about 1.1, alternatively from about 0.9 to about 1.0.

The fatty acid feedstock is provided to the reactor at a temperature above the melting point of the feedstock, i.e. the feedstock is provided as a liquid. The sulfonation is conducted such that the reaction mass is maintained as a mobile liquid throughout the course of reaction. Preferably, a means of cooling the reaction mixture during the course of contact between the feedstock stream and the gaseous $SO_3$ stream is provided so that the sulfonic acid product is produced from the reactor at a temperature of from about 10° C. to about 80° C., alternatively from about 20° C. to about 60° C., alternatively from about 30° C. to about 60° C.

Sulfonated unsaturated fatty acid salt and sulfonated hydroxy fatty acid salt products include, for example, those sold in Europe as Polystep® OPA by Stepan Company, and as Lankropol OPA and Lankropol OPA-V by Akzo Nobel, and in the United States as Calsoft™ OS-45S by Pilot Chemical.

SE is produced from the sulfonation step and comprises carboxylic esters, provided that the reaction conditions are sufficient, for example a high enough temperature of the acid stream, to promote carboxylic ester formation. While not limiting the scope of the presently described technology, the temperature at which carboxylic ester formation may occur is greater than about 10° C., alternatively greater than about 20° C., alternatively greater than about 30° C. The sulfonic acid products may further comprise sulfonic acid esters, including but not limited to cyclic esters, i.e., sultones.

The SE produced from sulfonation can be immediately transferred to a vessel or reactor, for example a continuous neutralizer ("CN"), for the purpose of neutralizing sulfonic acids and at least a portion of the carboxylic acids that are present. Alternatively, aging of the SE sulfonic acid may be provided for the purpose of modifying the composition of the acid, particularly with regard to an increase in the amount of esters wherein X and Y within one or more repeating units, in Formula 1, are both H. Neutralization of the acids is accomplished by reaction with aqueous base, for example but not limited to aqueous NaOH, KOH, ammonium hydroxide, and metal carbonates. Combinations of two or more salts, such as mixed sodium and potassium salts in any proportions, are contemplated. As explained in further detail below, particular ratios of mixed potassium and sodium salts can provide mixed salt compositions of the present technology that have improved phase stability as compared to compositions comprising only the sodium salt or potassium salt. In some embodiments, the amount of alkali that may be used in the neutralization is an amount that provides a neutralized product with a pH of about 4 to about 10. In these embodiments, the neutralized reaction mass may be produced in a way that minimizes the hydrolysis of carboxylic esters. In at least some of these embodiments, the amount of carboxylic ester hydrolysis that may occur may approach zero. When utilized, the CN may be operated with a mass fraction of acid of from about 0.1 to about 0.8, optionally about 0.5. The process can be carried out at a temperature of about 20 to about 100° C., alternatively about 40 to about 70° C.

Neutralization of the SE sulfonic acid may be conducted using an amount of aqueous base that is sufficient to neutralize all free acid functionality in the SE product, including carboxylic acids, and is sufficient to provide an excess of free caustic that is available to further react for the purposes of sultone hydrolysis, sulfonic acid anhydride hydrolysis, sulfonic carboxylic acid ester hydrolysis, and a desired amount of carboxylic ester hydrolysis, provided that adequate time and temperature for ester hydrolysis is subsequently provided. In one embodiment of this aspect, the amount of base is sufficient to enable from about 1% to about 95% hydrolysis of carboxylic esters. In another embodiment of this aspect, the amount of alkali is sufficient to enable hydrolysis of greater than about 95% of carboxylic esters, alternatively practically all carboxylic esters present in the sulfonic acid intermediate. In this embodiment, the resulting product that can be obtained by subsequently providing adequate time and temperature for ester hydrolysis to occur has a carboxylic ester content that may correspond to, for example, less than about 5%, alternatively less than about 2%, alternatively less than about 1% of the total carboxylic functionality in the composition. In these ways, EHP and PEHP can be produced.

Hydrolysis of Sultones

In one aspect of the presently described technology wherein a neutralized SE is produced with a pH of from about 4 to about 10, the neutralized product can be subjected to a hydrolysis step for the purpose of hydrolyzing sultones, sulfonic acid esters, and acid anhydrides. This sultone hydrolysis step may be conducted under conditions that prevent significant hydrolysis of carboxylic esters in the resultant product. The temperature of the sultone hydrolysis reaction mixture may be from about 20° C. to about 140° C., alternatively from about 50° C. to about 90° C. In some embodiments, the pH of the reaction mixture may be maintained in the range of about 4 to about 10 throughout the course of reaction without the need to add additional caustic. In some additional embodiments, additional caustic may be added to ensure that the pH is maintained in the range of about 4 to about 10. The sultone hydrolysis may be conducted in a continuous or batch process method and may be conducted for an amount of time necessary to result in a stabilized level of free alkalinity, as may be judged, for example, by titration to bromophenol blue endpoint with aqueous HCl.

It is contemplated that hydrolysis of sultones may be conducted at a pH above about 10 without substantial carboxylic ester hydrolysis provided that the reaction temperature and free caustic are maintained sufficiently low.

Hydrolysis of Carboxylic Esters

In one aspect of the presently described technology, carboxylic esters present in SE and optionally SHP may optionally be subjected to an alkaline hydrolysis step for the purpose of converting carboxylic esters into carboxylates to afford EHP and/or PEHP. This ester hydrolysis step may be conducted concurrently with a step to hydrolyze sultones or in a subsequent separate step. The ester hydrolysis step may be conducted in a batch, semi-batch, or continuous reaction mode. For example, the ester hydrolysis may be conducted in a stirred tank reactor, a loop reactor, a plug flow reactor, a single or multi-stage continuous stirred tank reactor, or any other reactor that can provide adequate temperature and time to afford an ester hydrolyzed product. Alkaline hydrolysis of the carboxylic esters may be conducted at a temperature of about 20° C. to about 150° C., alternatively about 50° C. to about 150° C., alternatively about 70° C. to about 150° C. In one non-limiting example, the ester hydrolysis is conducted at about 85° C. for about 4 hours.

The pH of the reaction mixture during the ester hydrolysis reaction, as measured on diluted samples, for example about 1 wt % of sample diluted in water, is greater than about 9.5, optionally greater than about 10. Since free caustic is consumed by the ester hydrolysis reaction, sufficient caustic is preferably provided to maintain the pH of reaction mixture above about 9.5. The amount of caustic that may be used in the ester hydrolysis step is preferably greater than the amount of caustic required to neutralize any free acid that may be present in the reaction mass, including carboxylic acids, and to hydrolyze sultones, sulfonic acid esters and anhydrides that may be present. In a given reaction mass, the amount of free caustic that may be available to hydrolyze carboxylic esters may be measured, for example, by potentiometric titration of an aliquot of reaction mass diluted in water with aqueous HCl to an endpoint between a pH of about 9 to about 10. In some embodiments, an amount of free caustic is provided that is sufficient to hydrolyze from about 1% to about 100% of carboxylic esters present in SE. If so desired, a substantial excess of free caustic relative to carboxylic ester content may be used in order to ensure a very high degree of ester hydrolysis.

In another aspect of the presently described technology, carboxylic esters present in SE may be hydrolyzed with water under acidic conditions. For example, it is contemplated that the degree of ester hydrolysis may be controlled by the amount of water that is mixed with the SE sulfonic acid, the reaction temperature, and the reaction time. Complete and partial ester hydrolysis of carboxylic esters by this method is contemplated.

It is further contemplated that the sultones, sulfonic acid esters, and/or anhydrides present in SE sulfonic acid products may be hydrolyzed with water under acidic conditions. It is contemplated that suitable reaction conditions will allow the hydrolysis of sultones, sulfonic acid esters, and/or anhydrides, and any other species that may be susceptible to acid hydrolysis to occur with or without hydrolysis of carboxylic esters.

Neutral Bleaching

In at least one embodiment, bleaching of neutralized products of SE may be conducted by treating the products with aqueous hydrogen peroxide, for example about 35% $H_2O_2$, in a bleaching reaction that is conducted at a temperature of about 20° C. to about 150° C., alternatively about 50° C. to about 120° C., alternatively about 70° C. to about 100° C. Alternatively, metal hypochlorite, ozone, or any other oxidant or other material that is effective as a bleaching agent may be used. The hydrogen peroxide or alternative oxidizing agent may be used in any amount that is effective in providing a desired color reduction. For example, aqueous hydrogen peroxide may be added to provide about 0.05% to about 5% by weight active hydrogen peroxide, alternatively from about 0.1% to about 3%. The bleaching of the neutralized product may be conducted in the same step as the sultone hydrolysis, or may be conducted in a separate step. For example, if carried out concurrently, hydrogen peroxide can be added at about 2% (wt/wt) concentration (at 100% active) to a reaction vessel used to conduct sultone hydrolysis. The free alkalinity and free peroxide can be measured periodically until the targeted % free alkalinity level, for example about 1.8% to about 2.0% is reached. If the % free alkalinity is lower than the target before sultone hydrolysis is complete, then an additional amount of base can be added to maintain the target levels. In at least one embodiment, it is preferable that the amount of free peroxide in the reaction mixture be maintained above about 20 ppm, alternatively above about 50 ppm, alternatively above about 100 ppm, alternatively about 200 ppm, alternatively about 300 ppm, alternatively about 400 ppm, alternatively above about 500 ppm, so as to avoid discoloration of the reaction mass, adding additional amounts of hydrogen peroxide if necessary.

If required or desired, additional hydrogen peroxide can be added after sultone hydrolysis is completed for the purpose of enabling additional bleaching of the SHP. If required or desired, a reducing agent such as $SO_2$ or sulfurous acid, or metal salts thereof, can be added at or near the end of the bleaching step in order to reduce residual free peroxide to a desired level.

In accordance with some embodiments, it is preferable to conduct the bleaching of neutralized products of sulfo-estolides with hydrogen peroxide at a pH in the range of about 4.5 to about 7.5, alternatively about 5 to about 7, wherein these ranges correspond to pH values measured on diluted samples, for example about 1 wt % or about 2 wt % of sample diluted in water. Preferably, the pH of the bleaching reaction mixture is maintained, at least initially, below a pre-determined level that is necessary to minimize hydrogen peroxide decomposition, to prevent severe foaming of the reaction mixture, and to improve color reduction. It has been found that if the pH of the bleaching reaction mixture is at and above that pre-determined level, at least during the initial stage of bleaching reaction, substantial peroxide decomposition and severe foaming occurs. Without intending to be bound by any particular theory, it is believed that such decomposition and severe foaming may be dependent on a number of factors, including dissolved metal ions in the reaction mixture, exposure to metal reaction equipment surfaces, and bleaching reaction temperature. It is contemplated that the decomposition of bleaching agent may be altered or mitigated through the incorporation of stabilizers, including but not limited to metal chelating agents, or alternatively through the passivation of metal surfaces or the use of non-metal surface process equipment.

Adjusting pH to Improve Product Stability Against Inhomogeneity

In some preferred embodiments, a concentrated aqueous solution of SHP, PEHP, and EHP may be prepared in a process comprising at least the steps of sulfonating a feedstock comprising an unsaturated fatty acid, neutralizing the resulting SE sulfonic acid intermediate, and hydrolyzing sultones. In these preferred embodiments, it is preferable that the pH of the final concentrated aqueous solution to be stored, transported, and optionally handled in additional ways is maintained in a pH range that enables a clear, homogeneous liquid product, free of substantial precipitation or other physical form instability. Surprisingly, it has been discovered that specific pH ranges can lead to physical instability as characterized by precipitation of solids and/or separation of liquid product into two or more layers. Physical stability is also referred to in this application as "phase stability." Alternatively, a "phase-stable" product is a physically stable product that is a clear, homogeneous liquid product that is free of substantial precipitation or other physical form instability. Inorganic salt, nonsulfonated-estolide, and fatty acid levels can be controlled to provide a substantially precipitate free phase-stable physical form. The ratios of these components will be dependent upon the temperature and concentration of SE in the composition.

Improved Phase Stability Through Mixed Salts

It has surprisingly been found that the physical stability or phase stability of the final concentrated aqueous solution can also be improved by forming particular salt mixtures of SE, SHP, PEHP and EHP. For example, a final concentrated liquid product comprising a mixture of sodium and potassium salts of SHP in particular ratios surprisingly exhibits phase stability at a pH of about 6.5 or greater, whereas a pure sodium salt or pure potassium salt form of the product exhibits phase instability under the same product conditions. Such phase instability of single salt products can present problems during product processing as well as during storage and handling. For example, as discussed above, it is preferred to conduct the hydrogen peroxide bleaching of neutralized products of sulfo-estolides at a pH range of 4.5 to about 7.5, alternatively about 5 to about 7. However, although a pH range of about 5 to about 7.5 may be an optimal range for bleaching, a pH of greater than about 6.0 can lead to physical instability of an aqueous solution comprising only a single salt form of the sulfo-estolide, such as only the potassium salt or only the sodium salt of sulfo-estolide. Reducing the concentration of the aqueous solution can lead to a phase-stable product, but reducing the concentration is not an optimal solution to the phase stability problem because concentrated products are more desirable for ease of shipping and storage, and product formulation options. Concentrations of at least about 50% by weight actives, alternatively at least about 60% by weight actives are preferred.

In addition to the pH affecting phase stability, the presence of inorganic sulfates in the aqueous composition in amounts of about 2% by weight or greater can cause phase instability. For example, elevated sulfate levels of about 2% by weight or greater can cause salting out of the actives in the composition, resulting in phase instability. In addition to or alternatively, phase instability can be due to crystallization of the inorganic sulfate. Therefore, it is desirable to minimize the inorganic sulfate levels in order to achieve a phase-stable composition. Minimizing inorganic sulfate levels can be problematic, however, since inorganic sulfate is a byproduct of the addition of $SO_2$ or metal salts thereof to the SHP composition during or after bleaching to reduce residual free peroxide to a desired level. Since it is also desirable to decompose the peroxide in order to reduce the residual peroxide levels in the bleached product to less than about 0.5%, alternatively less than about 0.3%, alternatively less than about 0.2%, achieving a desired residual free peroxide level while minimizing the inorganic sulfate level can be difficult. One method of decomposing the peroxide is to gradually increase the pH of the composition by adding caustic, for example KOH or NaOH. However, increasing the pH to a pH of greater than about 6.0 can lead to phase instability of the composition.

One solution to the problem of maintaining phase stability of concentrated aqueous solutions of SE, SHP, PEHP and EHP is to form mixed potassium and sodium salt solutions of SE, SHP, PEHP and EHP.

Surprisingly, phase-stable concentrated aqueous solutions of SE, SHP, PEHP and EHP can be obtained by forming mixed salt solutions of SE, SHP, PEHP and EHP. For example, it has been found that phase-stable concentrated aqueous solutions of SHP can be obtained at pHs of greater than about 6.0 to about 8.5 and at inorganic sulfate levels of about 2% when mixtures of salts, for example a mixture of sodium and potassium salts of SHP are present in the aqueous solution in particular ratios. The mixtures of salts can be formed in different ways. For example, a mixture of NaOH and KOH can be used to neutralize the SE sulfonic acid intermediate. Alternatively, neutralized pure potassium salts can be mixed with neutralized pure sodium salts to form the mixture of salts. Another alternative method of forming the mixture of salts is to neutralize the SE sulfonic acid intermediate with either NaOH or KOH to form a single salt sulfoestolide, and then use the other of NaOH or KOH or a mixture thereof, to adjust the pH at any stage of the manufacturing process, such as, for example, during sultone hydrolysis, during carboxylic ester hydrolysis, during peroxide bleaching and decomposition, or even post-bleaching. Another alternative is to introduce the counterion with the metal salt of $SO_2$ that may be added at the end of the bleaching step to reduce residual free peroxide.

The particular amounts of sodium and potassium salts in the mixture that result in phase-stable compositions are dependent upon the particular pH, the concentration of the SE, SHP, PEHP or EHP in the composition, the amount of unsulfonated fatty acid present in the composition, and the amount of inorganic sulfate present. For example, at a pH of about 6.4, with a concentration of 64% by weight actives of SHP, an inorganic sulfate amount of 2% by weight and an amount of unsulfonated fatty acid present of 6.2% by weight, phase-stable compositions can be obtained when the weight fraction of potassium salt is about 0.5 to about 0.8 based on the total weight of the potassium and sodium salts. However, when the same composition in terms of concentration, amount of inorganic sulfate, and amount of unsulfonated fatty acid is at a pH of about 7.5, phase-stable compositions are obtained when the fraction of potassium salt is about 0.1 to about 0.5 based on the total weight of the potassium and sodium salts. At a pH of about 8.5, phase-stable compositions are obtained when the fraction of potassium salt is about 0.3 to about 0.4 based on the total weight of the potassium and sodium salts. It will be appreciated by at least those skilled in the art that phase-stable compositions of mixed potassium and sodium salts can be obtained at other pH values (for example pH values of about 6.0 to about 6.3, about 6.5 to about 7.4, about 7.6 to about 8.4, and greater than about 8.5). It will also be appreciated that phase-stability of the mixed salt compositions can be achieved through pH adjustment and/or adjustment of the particular amounts of the potassium and sodium salts in the mixture.

In contrast to the mixed salt compositions, pure potassium salt and pure sodium salt forms of the compositions under identical conditions are not phase-stable at any pH in the range of about 6.4 to about 8.5. Providing compositions comprising mixed salts of SE, SHP, PEHP and EHP in particular ratios results in phase-stable compositions and therefore quite surprisingly and unexpectedly provides an advantage and improvement over compositions comprising only a single salt form of the SE, SHP, PEHP or EHP.

In addition to improved phase stability, sodium and potassium mixed salt compositions of the present technology can provide reduced viscosity at room temperature (e.g. about 20° C.) compared to the viscosities of compositions comprising the pure sodium salt or pure potassium salt. It has surprisingly been found that mixtures containing a fraction of potassium salt of about 0.8 to about 0.9 based on the total weight of the potassium and sodium salts have viscosities of about 1500 to about 1540 centipoise, whereas, under the same conditions, a sodium salt composition has a viscosity of over about 3000 centipoise and a potassium salt composition has a viscosity of about 1640. Viscosities for each of these compositions are measured at 20° C. at a sheer rate of 10 $sec^{-1}$. Lower viscosities at room temperature (e.g. about 20° C.) for the mixed sodium and potassium salt compositions provide advantages such as improved formulation into cold-mix applications.

It is anticipated that SE, SHP, PHEP and EHP compositions that are comprised of mixed salts other than or in addition to sodium/potassium mixed salts will display beneficial properties relative to single salt compositions. As a non-limiting example, mixed salt compositions comprising ammonium or substituted ammonium salts and alkaline or alkaline earth metal salts may exhibit improved phase-stability, higher solubility, improved comparability in multi-ingredient formulations, lower viscosity, and/or other advantageous properties as compared to the individual single salt forms.

Acid Bleaching

One way to reduce color is by bleaching SE sulfonic acid before neutralizing, which can be referred to as acid bleaching. Acid bleaching of SE may have the advantage, by itself or in combination with additional bleaching after neutralization, of reducing the color of SE more than would normally be achieved by neutral bleaching as described above. Acid bleaching may be carried out, for example, by adding about 0.1% to about 8% active $H_2O_2$, alternatively about 0.5% to about 4% active $H_2O_2$, providing for inclusion of water at a level of about 0.1% to about 50%, alternatively about 1% to about 25%, alternatively about 3% to about 12%, and maintaining the bleaching reaction temperature from about 20° C. to about 100° C., alternatively at about 50° C. A critical aspect to SE acid bleaching is the incorporation of water into the bleaching reaction mixture such that the total water in the sulfonic acid mixture is above a level that is necessary to stabilize the hydrogen peroxide in the reaction mixture and to afford an improved bleaching result.

In at least some preferred embodiments, wherein bleached SE sulfonic acid is converted to SHP, it is preferred to maintain peroxide at a level above about 100 ppm of hydrogen peroxide, alternately about 500 ppm, throughout the sultone hydrolysis reaction. Within these embodiments, it is additionally preferred to maintain the hydrolysis reaction mixture, at least initially, at a pH below about 7.5 alternatively about 7.0, wherein these values correspond to pH values measured on diluted samples, for example about 1 wt % or about 2 wt % of sample diluted in water. In at least some embodiments, it is preferable to maintain the sultone hydrolysis reaction mixture, at least initially, at a pH in the range of about 4.5 to about 7.5, alternatively about 5 to about 7, so as to enable additional bleaching of the reaction mixture during the sultone hydrolysis reaction.

In methods comprising the step of bleaching SE sulfonic acid with aqueous hydrogen peroxide to produce a bleached acid, the acid bleaching reaction mixture may further comprise about 1 to about 500 alternatively about 5 to about 100 ppm of a transition metal cation selected from the group $Fe^{2+}$, $Fe^{3+}$, $Mn^{2+}$, $Mn^{3+}$, and $Mn^{4+}$ for the purpose of providing for a substantial improvement in bleaching result and/or acceleration of the bleaching reaction. In addition or alternatively in these methods, aqueous base may be used as a source of water in the bleaching acid reaction mixture so as to enable the production of higher solids in the final SE salt product than can be achieved in comparable processes that utilize water instead of aqueous base. In at least some instances the use of aqueous base in the bleaching acid reaction mixture can substantially increase the stability of peroxide in the reaction mixture. In addition, it will be appreciated by at least those skilled in the art that it may be desirable to use an aqueous base that provides a counterion in order to form a mixed salt mixture that can increase the phase stability of the resulting composition of the present technology.

Product Descriptions

Not wanting to be bound by any particular theory, the compositions of the present technology defined by Formula 1, are now believed to be comprised of complex mixtures of compounds that are monomeric, dimeric, and higher-order oligomeric species in terms of the number of originating fatty acid chains. The oligomerization in these mixtures is via the formation of ester linkages. Branched oligomers are also contemplated.

The sulfo-estolide functional group corresponds structurally to the condensation of the hydroxyl group of an internal hydroxy sulfonate of fatty acid with the carboxylic acid group of a second fatty acid chain, wherein the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). The position of the sulfonate group along the back bone of the fatty acid chains is dictated by the location of the double bond in the starting material (9-octadecenoic acid for example) and the "direction" in which $SO_3$ adds across the double bond (thus, 9- and 10-sulfonate positions from oleic acid).

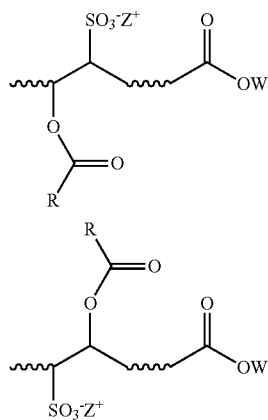

where R:

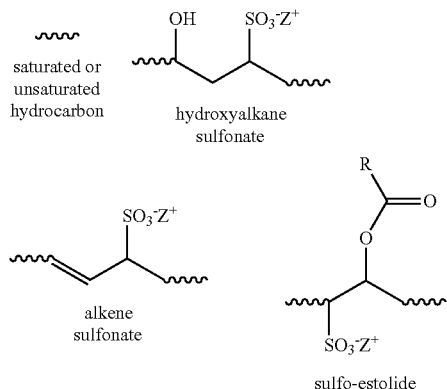

Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

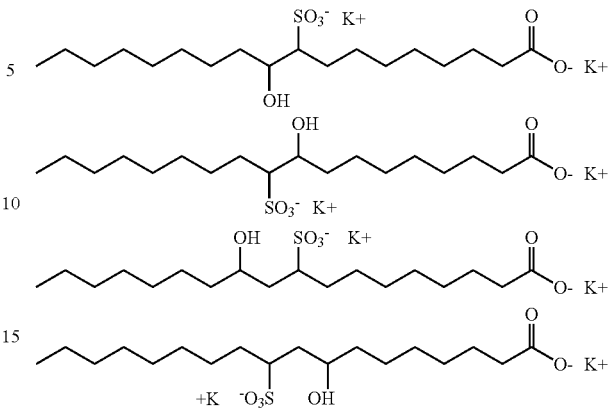

The monomeric components are further believed to comprise, in part, specific internal alkene sulfonates of fatty acid. These components may comprise cis- and/or trans-double bonds. It is also possible that compounds are present wherein the unsaturation is at the position of the sulfonate group (i.e., vinylic sulfonates). Examples are shown below.

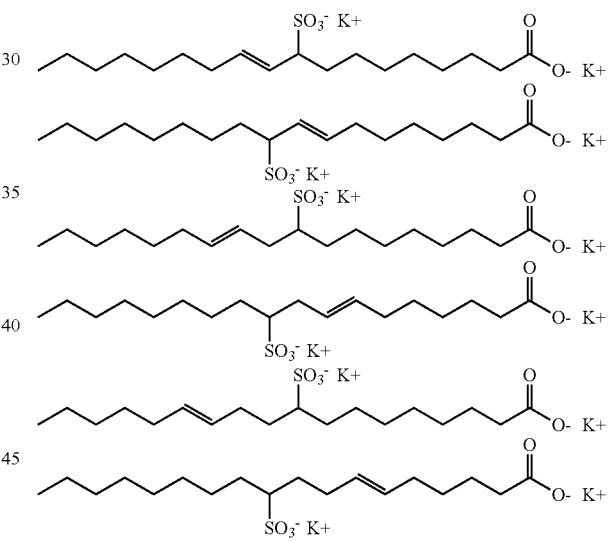

The monomeric components may further comprise disulfonated species, unsaturated fatty acids, and saturated fatty acids.

EHP is sometimes used herein as a designation for sulfonated products that have been subjected to complete hydrolysis of sulfo-estolide functionality. Such hydrolysis can be accomplished by, for example, treatment of SHP with excess base under high pH conditions (for example greater than about 11) at elevated temperatures (for example about 85° C. to about 100° C.). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C.

Rueggeberg, Journal of the American Oil Chemists Society (JAOCS), Volume 33, Number 9, September, 1956, pp 383-389.

It can also be appreciated that PHEP will be comprised of elevated amounts of monomeric hydroxyalkane sulfonates and alkene sulfonates while maintaining some level of sulfoestolide functionality.

Cleaning Products

Desirable surfactant attributes utilized in cleaning products, for example, include, among others, being in liquid form at room temperature, an ability to be formulated in cold-mix applications, and an ability to perform as well as or better than existing surfactants alone or when incorporated into comparable cleaning formulations/products.

Desirable attributes for the mixed salt SHP, PEHP or EHP compositions in HDL applications include, for example, the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming within detergent-based cleaning products. For example, for an HDL used in a high efficiency (it should be appreciated that all high efficiency ("HE") washing machines include all front loading washing machines as well) washing machine, low foam is desired to achieve the best cleaning and to avoid excess foaming which reduces and/or disrupts the cleaning process and/or machinery. Other desirable properties include the ability to clarify the formulation and to improve stability.

Formulation Viscosity

Formulations of the present technology are contemplated as having a viscosity of about 5 cPs (centipoise) to about 2000 cPs, measured at 25° C. using a Brookfield Viscometer model LV, having a spindle #2, set at a speed of about 5 rpm. Certain SHP, PEHP, or EHP formulations have been found to have lower viscosity than comparable formulations lacking these surfactants, so these compositions function as viscosity reducers, which is very useful for making the contemplated highly concentrated, (e.g. greater than about 40% surfactant active) detergent formulations.

Detergent Compositions

A wide variety of detergent compositions can be made that include mixed salt SE, PHSE, HSE, SHP, PEHP, EHP, or combinations of two or more of these, as described in the present application, with or without other ingredients as specified below. Formulations are contemplated including about 1% to about 99% SE, PHSE, HSE, SHP, PEHP, and/or EHP, more preferably between about 1% and about 60%, even more preferably between about 1% and about 30%, with about 99% to about 1% water or other suitable carrier/vehicle/diluent, and, optionally, other ingredients as described herein.

Surfactants

The detergent compositions can contain co-surfactants, which can be anionic, cationic, nonionic, ampholytic, zwitterionic, or combinations of these. Suitable co-surfactants for use in detergent compositions are described in application no. PCT/US09/31455 filed on Jan. 20, 2009, the disclosure of which is incorporated herein by reference.

Laundry Detergent Composition

Four desirable characteristics of a laundry detergent composition, in particular a liquid composition (although the present disclosure is not limited to a liquid composition, or to a composition having any or all of these attributes) are that (1) a concentrated formulation is useful to save on shelf space of a retailer, (2) a "green" or environmentally friendly (i.e., "eco-friendly") composition is useful, (3) a composition that works in modern high efficiency washing machines which use less energy and less water to wash clothes than previous machines is useful, and/or (4) a composition that cleans well in lower temperature water for example less than about 70° F.

To save a substantial amount of retailer shelf space, a concentrated formulation is contemplated having two or even three, four, five, six, or even greater (e.g., 8×) times potency per unit volume or dose as conventional laundry detergents. The use of less water complicates the formulation of a detergent composition, as it needs to be more soluble and otherwise to work well when diluted in relatively little water.

To make a "green" formula, the surfactants should be ultimately biodegradable and non-toxic. To meet consumer perceptions and reduce the use of petrochemicals, a "green" formula may also advantageously be limited to the use of renewable hydrocarbons, such as vegetable or animal fats and oils, in the manufacture of surfactants.

High efficiency (HE) washing machines present several challenges to the detergent formulation. As of January 2011, all washing machines sold in the US must be HE, at least to some extent, and this requirement will only become more restrictive in the coming years. Front loading machines, all of which are HE machines, represent the highest efficiency, are increasingly being used. Thus, it is desirable to have detergent compositions that can be used in such machinery. It is believed that the compositions and formulations of the present technology can be utilized in HE washing machines and achieve the unexpected properties and/or outcomes as described herein.

Further, heavy duty liquid (HDL) detergent formulas are impacted by HE machines because the significantly lower water usage requires that less foam be generated during the wash cycle. As the water usage levels continue to decrease in future generations of HE machines, detergents may be required to transition to no foam. In addition, HE HDLs should also disperse quickly and cleanly at lower wash temperatures.

To work in a modern high efficiency washing machine, a detergent composition needs to work in relatively concentrated form in cold water, as these washing machines use relatively little water and cooler washing temperatures than prior machines. The sudsing of such high-efficiency formulations must also be reduced, or even eliminated, in a low-water environment to provide effective cleaning performance. The anti-redeposition properties of a high efficiency detergent formulation also must be robust in a low-water environment. In addition, formulations that allow the used wash water to be more easily rinsed out of the clothes or spun out of the clothes in a washing machine are also contemplated, to promote efficiency.

Liquid fabric softener formulations and "softergent" (fabric softener/detergent dual functional) single-add formulations also may need to change as water usage continues to decline in HE machines. A washer-added softener is dispensed during the rinse cycle in these machines. The present mixed salt SE, SHP, PEHP, EHP, PHSE, and HSE compositions of the present technology can provide some softening activity, which is contemplated to address these problems.

The laundry detergents and additives containing the presently described mixed salt SE, SHP, PEHP, EHP, PHSE, and HSE compositions are contemplated to provide high concentration formulations, or "green" formulations, or formulations that work well in high efficiency washing machines. Such detergents and additives are contemplated that have at least one of the advantages or desirable characteristics specified above, or combinations of two or more of these advantages, at least to some degree.

In addition to the surfactants, a laundry detergent composition commonly contains other ingredients for various purposes, such as, for example, builders and alkaline agents, enzymes, and adjuvants. These ingredients are further described in application no. PCT/US09/31455 filed on Jan. 20, 2009, the disclosure of which is incorporated herein by reference.

Household, Institutional, Industrial Cleaning Products and/or Personal Care Products It is contemplated that the mixed salt SE, SHP, PEHP, EHP, PHSE and HSE compositions described herein can also be used in end-use applications including, but not limited to, household, industrial and institutional cleaning products, as well as personal care cleansing products.

For household, industrial and institutional cleaning products, both surfactants and solvents are important ingredients in these products. Desirable attributes for such products include, for example, the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming of different household, industrial and institutional products depending on the desired end-use applications. For example, a liquid manual dish washing detergent preferably has the ability to foam in the presence of soil that is being removed from dishware. Yet, for a dish washing detergent for use in an automatic dishwashing machine, low foam is desired to achieve the best cleaning and to avoid excess foaming. Other desirable properties of such consumer products include the ability to clarify the formulation and to improve stability. For hard surface cleaners, it is desirable to have the ability to wet various software types and couple or suspend soils to leave the surface free from residue in the form of streaking and/or filming.

The mixed salt compositions described herein can be incorporated into various compositions and used as surfactants, emulsifiers, skin feel agents, film formers, rheological modifiers, solvents, release agents, lubrication agents, conditioners, dispersants, and hydrotropes. In addition, the mixed salt SE, SHP, PEHP, EHP, PHSE and HSE compositions can be combined with other surfactants, additives and ingredients commonly contained in household, industrial and institutional cleaning products, and personal care products in order to prepare a wide variety of product formulations. These other surfactants, additives and ingredients are described in further detail in application no. PCT/US09/31608 filed on Jan. 21, 2009, which is herein incorporated by reference.

Forms

One or more compositions of the present technology can take any of a number of forms and any of the different delivery systems that are currently known or to be developed in the future such as ready-to-use, dilutable, wipes, sprays, gels, gel-packets, unit dose packages, etc.

For example, the compositions of the present technology can take the form of a dilutable fabric detergent or conditioner, that may be an isotropic liquid, a surfactant-structured liquid, a granular, spray-dried or dry-blended powder, a tablet, a paste, a molded solid, a water soluble sheet, or any other laundry detergent form known to those skilled in the art. A "dilutable" fabric detergent or conditioning composition is defined, for the purposes of this disclosure, as a product intended to be used by being diluted with water or a non-aqueous solvent by a ratio of more than 100:1, to produce a liquor suitable for treating textiles. "Green concentrate" compositions like those on the market today for Fantastic® (commercially available from SC Johnson of WI), Windex® (commercially available from SC Johnson of WI), and the like, can be formulated such that they could be a concentrate to be added to a bottle for final reconstitution.

The compositions of the present technology could also be formulated as a gel or a gel packet like the dishwasher products on the market today. Water soluble sheets or sachets, such as those described in U.S. Pat. Appl. No. 20020187909, which is incorporated herein by reference, are also envisaged as a potential form of the present technology. These may be sold under a variety of names, and for a number of purposes. The composition can also be deposited on a wipe, fabric, material, or other substrate.

Methods of Laundering Fabrics

Methods for laundering fabrics with SE, SHP, PEHP, EHP, PHSE or HSE-based formulations are contemplated. Such methods involve placing fabric articles to be laundered in a high efficiency washing machine or a regular (non-high efficiency) washing machine and placing an amount of the SE, SHP, PEHP or EHP-based composition sufficient to provide a concentration of the composition in water of from about 0.001% to about 5% by weight when the machine is operated in a wash cycle. A high efficiency machine is defined by the Soap and Detergent Association as any machine that uses approximately 20% to about 66% of the water, and as little as approximately 20% to about 50% of the energy, of a traditional, regular agitator washer (SDA "Washers and Detergents" publication 2005; http://www.cleaning101.com/laundry/HE.pdf. The wash cycle is actuated or started to launder the fabric articles.

EXAMPLES

The compositions and processes described herein, and ways to make and use them are illustrated by the following examples. Examples stated in the present or future tense are not represented as having been carried out.

Example 1

Preparation of SE Sulfonic Acid

The fatty acid feedstock used was derived from a vegetable oil source. For the purpose of sulfonation, the feedstock had an equivalent weight of about 270.6, as determined by iodine value. The feedstock was comprised of about 80% C-18:1, about 12.5% C-18:2, and about 7.5% saturated fatty acids, as measured by area count data obtained by gas chromatography using a flame ionization detector.

The feedstock was sulfonated on a falling film reactor using a feedstock temperature of about 15° C., an air/$SO_3$ temperature of about 40° C., a sulfonator jacket temperature of about 42° C., and a molar ratio of $SO_3$ to alkene functionality of about 1.0. After passing through a degassing unit, the acid produced from the sulfonation reaction was collected in small glass jars, frozen in an ice bath, and then stored in a freezer until further processing.

Analysis of Acid: The carboxylic acid content in the SE sulfonic acid product was determined by dissolving an aliquot of product in water that contained sufficient KOH to afford a solution with a pH greater than about 10.5. Titration of the solution with aqueous HCl indicated a free carboxylate content of about 2.04 milliequivalents per gram of sulfonated acid (meq/g). The sulfonic acid product was analyzed for carboxylic ester content by subjecting an aliquot of the acid to exhaustive alkaline hydrolysis conditions and then analyzing for carboxylate content. To accomplish this hydrolysis, an aliquot of product that was dissolved in dilute aqueous KOH was then digested for about 16 hours in an 85° C. oven, ensuring that the pH of the solution remained above about 10.5, and was then titrated with aqueous HCl. The carboxylate content, on the basis of starting sulfonic acid product mass, was thereby determined to be about 3.18 meq/g. The change in carboxylate content upon hydrolysis is attributable to the hydrolysis of carboxylic esters. Therefore, the amount of carboxylic ester functionality was found to be about 36 mol percent of the total carboxylic functionality (carboxylic acid+ carboxylic ester) present in the SE sulfonic acid product. $^1$H and $^{13}$C NMR spectra of the acid product dissolved in CDCl$_3$ displayed signals that are consistent with the structure of alpha-sulfo-estolide functionality. In addition, $^1$H NMR spectral data indicated that the SE sulfonic acid composition was further comprised of approximately 10 mol % of internal gamma sultones (1,3 dialkyl 1,3 sultones) relative to the total carboxylic functionality (carboxylic acid+ester).

Example 2

Preparation of Potassium Salts of SHP

The fatty acid feedstock used in this example had an equivalent weight of about 280 and was derived from a tallow source that typically affords fatty acids comprising about 70% C18:1, about 12% polyunsaturated acid, and about 10% to about 15% saturated fatty acid. The feedstock was sulfonated on a film reactor using a molar ratio of SO3 to alkene functionality of about 0.91. The sulfonic acid produced from the sulfonator was continuously neutralized in a loop reactor with aqueous KOH to produce a neutralized material that, when titrated to bromophenol blue endpoint with aqueous HCl, was analyzed as containing about 2.5% free alkalinity (base value, expressed in terms of wt. % KOH). If measured, the pH of this material, diluted in water, would be in the range of about 5.5 to about 7.5. The neutralized material was charged to a batch reactor and was then maintained at about 60° to about 65° C. in order to hydrolyze sultones, as well as any potential sulfonic acid esters and anhydrides that may be present in the material. During the hydrolysis, the base value was maintained in the range of about 1.5 to about 1.8%. The hydrolysis reaction was continued until base value remained constant. The pH of the final sultone hydrolyzed product (SHP) was about 5.6 to about 5.9. The solids level in the product was measured by gravimetric changes upon drying in a 105° C. oven and was found to be about 54% by weight. $^1$H NMR spectroscopy of an aliquot of the SHP indicated essentially complete hydrolysis of sultones and the presence of internal hydroxyalkane sulfonate groups that result from the hydrolysis of 1,3 dialkyl 1,3 sultones.

The SHP was characterized in terms of free carboxylic acid and potassium carboxylate functionality by titration with aqueous HCl. Titration of the product, as produced, indicated a carboxylate salt content of 0.25 milliequivalents per gram (meq/g). Titration of an aliquot that had been first adjusted to a pH of greater than about 10 with KOH indicated a carboxylate salt content of 0.78 meq/g. The difference between these two titration results corresponded to the unneutralized carboxylic acid content within the product, the calculated result being 0.53 meq/g. The carboxylic ester content within the product was then determined by first hydrolyzing the ester functionality at elevated temperature using excess caustic. To accomplish this hydrolysis, a 15 gram aliquot of product was mixed with 3 grams of 45% aqueous KOH in a vial and the resulting solution was digested in an 85° C. oven for several hours until measured carboxylate meq/g was observed to be constant. The change in carboxylate meq/g upon hydrolysis, correcting for dilution of the sample upon addition of caustic, was taken to be a quantitative measure of the carboxylic ester content in the product. Based on this process, the ester content was found to be 0.56 meq/g. Since the total amount of carboxylic acid, carboxylate salt, and carboxylic ester was found to add up to 1.34 meq/g, the molar percentage of fatty acid functionality in the composition that was present as carboxylic ester was calculated to be 42%.

The product was further characterized by $^1$H, $^{13}$C and 2D NMR spectroscopic methods on a JEOL ECA 500 spectrometer. A sample of the product was adjusted to pH 10 to ensure that all carboxylic acid functionality was converted to carboxylate salt form. An aliquot of this sample was then dried under vacuum to afford a semi-solid residue that was dissolved in D$_2$O. Quantitative $^{13}$C NMR spectroscopy demonstrated two sets of carbonyl carbons, in the ranges of about 184 to about 183 ppm and about 175 to about 173 ppm, corresponding to carboxylate (COO– K+) and carboxylic ester (COO-alkyl) functionality, respectively. The integrations of these two sets of peaks were in an approximate 6:4 ratio, respectively, consistent with approximately 40% of all carboxylic functionality in the product being present as carboxylic esters. 2D experiments provided evidence in both $^1$H and $^{13}$C spectra for the presence of substantial amounts alpha-sulfo-estolide functionality within the product mixture.

LC/MS$^n$ was used to further characterize the reaction product. Chromatographic separation on a reverse phase column revealed the presence of multiple components in the reaction product. Mass spectral data on some of these separated components provided evidence for the presence of sulfonated compounds that may be viewed as being comprised of two fatty acid chains, as well as sulfonated compounds that may viewed as being comprised of three fatty acid chains.

Example 3

Preparation of Sodium Salts of SHP

The fatty acid feedstock used in this example had an equivalent weight of about 270 and was derived from a vegetable oil source that typically affords fatty acids comprising about 80% C18:1, about 12% polyunsaturated acid, and about 8% saturated fatty acid. The feedstock was sulfonated on a film reactor using a molar ratio of SO$_3$ to alkene functionality of about 0.95 to produce SE sulfonic acid. This acid was continuously neutralized in a loop reactor with 50 percent (wt/wt) aqueous NaOH (caustic) and water, utilizing a mass ratio of about 0.68 of SE acid to about 0.16 of caustic to about 0.16 of water. The neutralized material that was collected off of the loop reactor in a batch reactor was then subjected to a sultone hydrolysis step by maintaining the liquid at 80° C. for 4 hours to produce sodium SHP. The pH of the SHP, measured by diluting a sample of the product with a 50/50 vol/vol mixture of water and isopropanol to a concentration of 2 wt %, was found to be 5.9. The SHP obtained was found to comprise 24.1% by weight of water, as determined by Karl-Fischer titration; 6.4 wt % unsulfonated fatty acid, as determined by gravimetric analysis of petroleum ether extractables (PEX) that were extracted from aqueous ethanol solutions at approximately pH 3; 2.1 wt % of sodium sulfate, as determined by titration of product in acidic aqueous acetone with lead perchlorate; and 67.4 wt % sulfo-estolide (actives), as calculated from mass balance.

Example 4

Preparation of Potassium Salts of SHP

The fatty acid feedstock used in this example had an equivalent weight of about 270 and was derived from a vegetable oil source that typically affords fatty acids comprising about 80% C18:1, about 12% polyunsaturated acid, and about 8% saturated fatty acid. The feedstock was sulfonated on a film reactor using a molar ratio of $SO_3$ to alkene functionality of about 0.95 to produce SE sulfonic acid. This acid was continuously neutralized in a loop reactor with 45 percent (wt/wt) aqueous KOH (caustic) and water, utilizing a mass ratio of about 0.60 of SE acid to about 0.23 of caustic to about 0.17 of water. The neutralized material that was collected off of the loop reactor in a batch reactor was then subjected to a sultone hydrolysis step by maintaining the liquid at 80° C. for about 4 hours. The SHP was concentrated by slow evaporation of water from the product at ambient conditions to produce a higher concentrated product (potassium SHP concentrate). The pH of the concentrate, measured by diluting a sample of the product with a 50/50 vol/vol mixture of water and isopropanol to a concentration of about 2 wt %, was found to be 6.0. The SHP obtained was found to comprise 21.0% by weight of water, as determined by Karl-Fischer titration; 6.1 wt % unsulfonated fatty acid, as determined by gravimetric analysis of petroleum ether extractables (PEX) that were extracted from aqueous ethanol solutions at approximately pH 3; 2.3 wt % of potassium sulfate, as determined by titration of product in acidic aqueous acetone with lead perchlorate; and 70.6 wt % sulfo-estolide (actives), as calculated from mass balance.

Example 5

Partial Ester Hydrolysis of SHP to Produce PEHP

To a quart (1-liter) jar was added about 824 g of the SHP of Example 2 and about 82.5 g of 45 wt. % aqueous KOH, which corresponded to a molar amount of KOH necessary to: (a) neutralized all free carboxylic acid; and (b) to hydrolyzed a portion of the carboxylic esters in the SHP with 0.50 molar equivalents of free caustic. The contents were thoroughly mixed and then the jar was sealed and placed in an approximately 85° C. oven for about 24 hours. Upon cooling, the obtained PEHP was homogeneous, free of precipitation or solids, and was a highly flowable liquid. The PEHP was analyzed by titration with aqueous HCl and was found to comprise about 0.96% meq/g of potassium carboxylate. Based on the mass balance from the reagent charges for the ester hydrolysis reaction and the change in carboxylate content, the degree of ester hydrolysis was calculated to be about 50.5 mol percent. At this level of ester hydrolysis, the carboxylic ester content in the PEHP was calculated to about 21 mol percent of total carboxylic functionality in the PEHP.

Examples 6-9

Preparation of Potassium Salts of SHP from Mixtures of Oleic Acid with Saturated Fatty Acids In these examples, which are summarized in Table 1, mixtures of unsaturated and saturated fatty acids were subjected to the sequential process steps of sulfonation with $SO_3$ on a film reactor to produce SE sulfonic acid, continuous neutralization of the sulfonic acid in a loop reactor, and hydrolysis of sultones in a batch reactor to produce SHP. The saturated fatty acids were incorporated to function as chain termination agents in the esterification reactions that may otherwise lead to substantial levels of oligomeric products such as compositions of Formula 1 where n=2 or more. In the sulfonation step, the feedstock temperature of about 25° C., an air/$SO_3$ temperature of about 41° C., and a sulfonator jacket temperature of about 25° C. are employed.

The oleic fatty acid used to prepare the fatty acid mixtures had an equivalent weight for the purpose of sulfonation of about 274.6, as determined by an iodine value of 92.4, and was comprised of about 78% C-18:1, about 12% C-18:2, and about 9% saturated fatty acids. The coconut fatty acid used to prepare the fatty acid mixtures in Examples 6, 7, and 8 had an iodine value of 2.1, and was comprised of approximately 8% C-8, approximately 6% C-10, approximately 51% C-12, approximately 19% C-14, approximately 9% C-16, and approximately 3% C-18 saturated fatty acids. The capric acid used to prepare the fatty acid mixture in Example 9 had an iodine value of about 0.2 and was comprised of about 99% $C_{10}$ saturated fatty acid.

The SHP samples produced were analyzed for carboxylic ester content as follows. Total meq/g of carboxylic acid and carboxylate salt in SHP was determined by titration of a sample, adjusted to pH of greater than about 11, with 0.1 N HCl. Total meq/g of carboxylic acid, carboxylate salt, and carboxylic ester in SHP was determined by 0.1 N HCl titration of a sample that had been exhaustively hydrolyzed with excess KOH at 85° C. for 16 hours. The mole percentage of total carboxylic functionality that was present as carboxylic esters in the SHP was then calculated. The SHP of Example 7 was further analyzed in terms of gravimetric analysis of petroleum ether extractables (PEX) that were extracted from aqueous ethanol solutions at approximately pH 3. These gravimetric analyses were conducted on separate aliquots before and then after a step of exhaustive ester hydrolysis that was conducted by means of incubation with excess KOH at 85° C. for 16 hours. The change in PEX before and after ester hydrolysis was then used to calculate an estimated degree of incorporation of non-sulfonated fatty acids into the SHP, as summarized in Table 1. $^1$H NMR analyses of the PEX samples indicated that both extracts consisted essentially of about 90 mol percent saturated fatty acid and about 10 mol percent monounsaturated fatty acid. This result confirmed that of a significant level (approximately 40 percent) of the coconut fatty acid (chain termination agent) was incorporated into the SHP as carboxylic esters.

TABLE 1

|  | Example 6 | Example 7 | Example 8 | Example 9 |
|---|---|---|---|---|
| Chain Termination Agent | Coconut Fatty Acid | Coconut Fatty Acid | Coconut Fatty Acid | Capric Acid |
| weight fraction of vegetable oleic acid in fatty acid feedstock | 0.80 | 0.68 | 0.68 | 0.65 |
| weight fraction of Chain Termination Agent in fatty acid feedstock | 0.20 | 0.32 | 0.32 | 0.35 |
| molar ratio of $SO_3$ to alkene functionality | 0.95 | 0.95 | 0.75 | 0.95 |
| wt fraction SE sulfonic acid in neutralization | 0.303 | 0.260 | 0.338 | 0.301 |
| wt fraction 45% aq. KOH in neutralization | 0.124 | 0.130 | 0.136 | 0.133 |
| wt fraction additional water in neutralization | 0.573 | 0.610 | 0.525 | 0.566 |
| pH (2 percent SHP solution (wt/wt) in $H_2O$ | 6.6 | 8.5 | 6.7 | 6.7 |
| percent solids (gravimetric, 105° C. oven for 2 hours) | 34.9 | 31.0 | 34.6 | 33.9 |
| Ester Content (mole percent carboxylic esters relative to total carboxylic functionality) | 36.6 | 33.5 | 30.2 | 29.1 |
| weight percent petroleum ether extractables in SHP (wt/wt total solids) |  | 18.76 |  |  |
| weight percent petroleum ether extractables after exhaustive ester hydrolysis (wt/wt total solids, corrected for dilution with caustic) |  | 31.61 |  |  |
| Percentage of non-sulfonated fatty acids that was incorporated into SHP as carboxylic esters |  | 40.7 |  |  |

Example 10

Ester Hydrolysis of SHP with Excess KOH to Produce EHP

An approximately 54% solids solution of the potassium salts of SHP, was prepared as described in Example 2. To a small vial was added about 15.0 g of this product and about 3.0 g of about 45 wt. % aqueous potassium hydroxide, which corresponded to a roughly 1.5 times the amount of caustic required to neutralize free carboxylic acids and to hydrolyzed carboxylic esters in the SHP. The contents of the vial were thoroughly mixed and then the vial was sealed and placed in an 85° C. oven for about 16 hours. Upon cooling, the obtained EHP was homogenous, was free of precipitation or solids, and was a highly flowable liquid. NMR analysis of the EHP indicated that there was no detectable carboxylic acid ester functionality, as judged by a lack of $^{13}C$ signals for ester carbonyl and by a lack of $^1H$ and $^{13}C$ signals that had been identified in the starting material as being consistent with alpha-sulfo estolide functionality. In addition, $^1H$ NMR data indicated hydroxyalkane sulfonate functionality that is signatured by a signal at about 3.9 ppm and that results from the hydrolysis of sulfo-estolide functional groups, at a level of about 38 mol percent relative to total carboxylic functionality. The spectroscopic analysis of the EHP was consistent with the product comprising a mixture of saturated and unsaturated monomeric fatty acid carboxylates, alkene sulfonate-functionalized fatty acid carboxylates, and hydroxy sulfonate-functionalized fatty acid carboxylates.

Example 11

Preparation of a Bleached Aqueous Concentrate of SHP Potassium Salts

The feedstock used in this example had an equivalent weight of about 274.6 and was comprised of about 78% C-18:1, about 12% C-18:2, and about 9% saturated fatty acids. The feedstock was sulfonated on a falling film reactor at a rate of about 129.3 lbs per hour using a molar ratio of $SO_3$ to alkene functionality of about 0.95. The SE sulfonic acid was continuously neutralized in a loop reactor with concurrent addition of about 51.1 lbs per hour of 45% aqueous KOH and about 46.5 lbs per hour of water. The temperature of the reaction mixture in the loop reactor was about 85° C. Neutralized SE solution was continuously fed from the loop reactor to an in-line mixer, where about 4.9 lbs per hour of 50% aqueous hydrogen peroxide was homogenized into the solution, which was about pH 5.5. This reaction mixture was then fed to a stirred tank reactor. After collecting about 60 gallons of reaction mixture, concurrent sultone hydrolysis and bleaching were continued at about 80° C. for about 4 additional hours, adding additional 45% aqueous KOH as necessary to maintain the pH of the reaction mixture in the range of about 5.2 to about 6.2. The SHP produced from this reaction was at a pH of about 6.2, was comprised of about 70.5% solids and about 0.5% (wt/wt) active peroxide, and had a Klett color at 1 percent solids concentration of 20.

Example 12A-D

Impact of pH on Bleaching of SHP With Hydrogen Peroxide

An approximately 73% solids solution of SHP was produced from vegetable oil-derived oleic acid (equivalent weight of about 274.6) by sulfonation on a film reactor at a molar ratio of $SO_3$ to alkene functionality of about 0.95, neutralization with aqueous KOH with a loop reactor, and sultone hydrolysis in a batch reactor. The SHP was obtained at a pH of about 5.25, measured at a concentration of 2 wt % of SHP solution diluted with deionized water. Color was measured on solutions of 5 wt % of SHP solution diluted with deionized water using a Klett-Summerson photoelectric colorimeter equipped with a 4 cm pathlength glass cell. The Klett color of the diluted unbleached SHP at was 729. pH of the SHP was adjusted to several different values by the addition of 45% aqueous KOH. Bleaching of the SHP was conducted at about 85° C. using 3 percent active $H_2O_2$ (wt/wt), provided to the reaction mixture in the form of 35% aqueous $H_2O_2$. pH values of the bleaching reaction mixtures were observed to drift slightly downward by about 0.2 to about 0.4 pH units. Results from the bleaching reactions are summarized in Table 2. The reaction corresponding to entry 12D demonstrated a rapid decomposition of hydrogen peroxide, as evidenced by severe and rapid foaming of the reaction mass. This result demonstrates the importance of maintaining pH below a level necessary to minimize hydrogen peroxide decomposition, so to prevent severe foaming of the reaction mixture.

TABLE 2

| Entry | 12A | 12B | 12C | 12D |
|---|---|---|---|---|
| Initial pH (measured at 2 wt % SHP diluted in $H_2O$) | 5.25 | 6.2 | 6.5 | 6.9 |
| Bleached SHP Klett color (5 wt % solids in $H_2O$) | 105 | 93 | 93 | Not measured |
| Extent of reaction foaming (% volume expansion) | <5 | <5 | ~50 | >100: Foamed out of reactor |

Examples 13-14

Influence of pH on the Physical Stability of SHP Solutions

The influence of pH on the physical stability of SHP at ambient conditions (approximately 22° C.) was assessed by means of visual observation and measurement of sample turbidity. For the purposes of these examples, a physically stable sample was defined as a material that was a clear, homogeneous liquid product, free of precipitation of solids or separation of two or more fluid phases, as could be confirmed in terms of a turbidity reading of less than 20 NTU. Sample turbidity was measured on un-diluted samples using a HF Scientific Micro 100 Laboratory Turbidimeter equipped with a 30 mL cuvette. Samples were prepared by adjusting pH with aqueous KOH, as indicated in Table 3. pH was measured on 2 wt % SHP solutions diluted with de-ionized water. The results in Table 3 demonstrate that the physical stability of SHP samples can be improved by adjusting the pH to a value that is above, or alternatively below, a range of pH values that otherwise may result in physical separation and inhomogeneity of the product.

TABLE 3

| Example 13 SHP of Example 12 prior to bleaching: ~73% solids | | Example 14 SHP of Example 8 ~35% Solids | |
|---|---|---|---|
| pH | Appearance | Turbidity (NTU) | pH | Appearance | Turbidity (NTU) |
| 5.3 | Clear | 0.7 | 6.1 | Clear | 2.6 |
| 6.2 | Opaque, with precipitation | 550 | 6.7 | Opaque, with precipitation | >1000 |
| 6.9 | Opaque, with precipitation | >1000 | 9.0 | Clear | 9.0 |
| 7.8 | Opaque, with precipitation | >1000 | | | |
| 8.3 | Clear | 0.6 | | | |

Example 15

Influence of Mixed Salts on the Physical Stability of Concentrated SHP Solutions The influence of mixed sodium and potassium salts on the physical stability of SHP was assessed by means of visual observation of sample turbidity after sample storage at ambient conditions (approximately 22° C.) for at least two weeks. For purposes of this example, a physically stable sample was defined as a material that was a clear, homogenous liquid product, free of precipitation of solids or separation of two or more fluid phases. Separate portions of the sodium SHP of Example 3 and the potassium SHP concentrate of Example 4 were adjusted to obtain stock samples at pH values of about 6.0, 6.4, 7.5, and 8.5 (measured at 2 wt % concentration in 50/50 vol/vol water and isopropanol) by the addition of water, base, inorganic sulfate, and fatty acid so as to comprise about 2 wt % inorganic sulfate, about 6.1 wt % unsulfonated fatty acid, and about 64 wt % actives. Mixed salt samples were prepared by mixing appropriate ratios of these sodium and potassium stock samples on a weight basis, as indicated in Table 4, and heating to 50° C. for about 17 hours. Following heating, the samples were allowed to sit at ambient conditions for at least 2 weeks and then evaluated for phase stability. The results are shown in Table 4.

TABLE 4

| Wt. Fraction of Sample as K Salt SHP | Wt. fraction of total cation as $K^+$ | Mole fraction of total cation as $K^+$ | pH 6.0 | pH 6.4 | pH 7.5 | pH 8.5 |
|---|---|---|---|---|---|---|
| 0.0 | 0 | 0 | Stable | Instable | Instable | Instable |
| 0.1 | 0.13 | 0.08 | | Instable | Stable | Instable |
| 0.2 | 0.25 | 0.16 | | Instable | Stable | Instable |
| 0.3 | 0.36 | 0.25 | | Instable | Stable | Stable |
| 0.4 | 0.47 | 0.34 | | Instable | Stable | Stable |
| 0.5 | 0.57 | 0.43 | Stable | Stable | Stable | Instable |
| 0.6 | 0.66 | 0.54 | | Stable | Instable | Instable |
| 0.7 | 0.75 | 0.64 | | Stable | Instable | Instable |
| 0.8 | 0.84 | 0.75 | | Stable | Instable | Instable |
| 0.9 | 0.92 | 0.87 | | Instable | Instable | Instable |
| 1.0 | 1 | 1 | Stable | Instable | Instable | Instable |

The results in Table 4 demonstrate that the stability of SHP samples can be improved by mixing different salts of SHP in particular ratios depending upon pH. Pure sodium and pure potassium salts of SHP were not stable at pH values of about 6.4, 7.5 or 8.5, whereas mixtures of sodium and potassium salts could form phase-stable solutions at each of these pH values.

Example 16

Preparation of Mixed Sodium and Potassium Salts of SHP

A fatty acid feedstock comprising about 80 percent C18:1 fatty acid is sulfonated with gaseous $SO_3$ on a film reactor using a molar ratio of $SO_3$ to alkene functionality of about 0.95 to produce SE sulfonic acid. The acid is neutralized with a 1.5 K/Na molar ratio of aqueous sodium and potassium hydroxide. The neutralized material is collected and subjected to heating at a temperature of about 85° C. for about 4 hours to hydrolyze sultones. A mixed sodium and potassium salt SHP is obtained comprising about 64% (wt/wt) of sulfoestolide actives that exhibits a pH of about 6.5 for a 2% solution of the product dissolved in 50/50 (vol/vol) water and isopropanol. Upon cooling and storage for several weeks at 20° C., the SHP will remain as a clear, homogenous liquid product, free of precipitation of solids or separation of two or more fluid phases.

Example 17

For the following cleaning experiments, about 60 grams (g) of heavy duty liquid (HDL) was added to 90 F water in a high efficiency (HE) Whirlpool Duet Sport machine on Normal setting (54 minutes full cycle). Two runs per HDL, with 4 stain cloths per run, were carried out. Experimental stain cloths employed include: grass on cotton (purchased from scientific Services, Sparrow Bush, N.Y.), and, EMPA106 (purchased from Testfabrics, West Pittston, Pa.). Each wash also included 6 pounds of cotton, pillowcase ballast. At the end of each wash, the stain cloths were static dried and then L, a, b readings taken on a HunterLab LabScan XE spectrophotometer. L, a, b readings are also taken of the clean, unsoiled cotton fabric from which each stain was applied. Cleaning was then calculated by the following equation (as reported in the literature—Neiditch, O. W., et al, Journal of the American Oil Chemist's Society, December, 1980, 426):

$$SRI = 100 - \sqrt{(L_{clean} - L_{washed})^2 + (a_{clean} - a_{washed})^2 - (b_{clean} - b_{washed})^2}$$

where the SRI is the Stain Removal Index.

In this example, the cleaning benefits of using mixtures of sodium and potassium sulfo-estolide salts in HDL detergent formulations are demonstrated. The potassium and sodium SHP salts were made in accordance with Examples 4 and 3, respectively. The following HDL compositions were made:

TABLE 5

| Ingredient | Weight % Inclusion (100% active) | | | |
|---|---|---|---|---|
| | Formula 1 | Formula 2 | Formula 3 | Formula 4 |
| Potassium SHP | 15.0 | | 6 | 10.5 |
| Sodium SHP | | 15.0 | 9 | 4.5 |
| $C_{12-15}EO_7$* | 5.0 | 5.0 | 5.0 | 5.0 |
| Monoethanolamine | 1.0 | 1.0 | 1.0 | 1.0 |
| Triethanolamine | 1.0 | 1.0 | 1.0 | 1.0 |
| Sodium Citrate | 1.0 | 1.0 | 1.0 | 1.0 |

TABLE 5-continued

| Ingredient | Weight % Inclusion (100% active) | | | |
|---|---|---|---|---|
| | Formula 1 | Formula 2 | Formula 3 | Formula 4 |
| Water | 77.0 | 77.0 | 77.0 | 77.0 |
| pH | | | 10.0 | |

*BIO-SOFT® N25-7, Stepan Company, Northfield, IL.

Cleaning results are shown in Table 6.

TABLE 6

| Stain Cloth | SRI | | | |
|---|---|---|---|---|
| | Formula 1 | Formula 2 | Formula 3 | Formula 4 |
| Grass on cotton | 76.8 | 80.4 | 81.6 | 82.9 |
| EMPA 106 | 68.3 | 68.8 | 69.2 | 69.0 |

These results demonstrate that the potassium and sodium mixed salt SHPs used in HDL Formula 3 and Formula 4 afford superior cleaning on these stains compared with either of the single salt potassium SHP (Formula 1) or single salt sodium SHP (Formula 2) HDL formulations.

Examples 18A-J

Premium to Mid-Tier Laundry Detergent Formulas Employing Mixed Salt SEs

The following prophetic formulas in Table 7, are intended to cover liquid laundry detergent formulas. Unless more narrowly defined in the table, the pH of these formulas is between about pH 7 and about pH 10, preferably between about 7.5 and about 9.5 and most preferably between about 8.5 and about 9.0. In each case, these are intended to be liquid detergent formulas and, after the addition of optional ingredients, water would be used to bring the total weight up to 100%. The ingredients are listed on a "100% Active" basis, meaning that the listed weight percentage is not diluted but rather 100% of the ingredient.

TABLE 7

| Ingredient* | Generic Formula | % Inclusion by Weight (Based on 100% Active) | | | | | | | | | |
|---|---|---|---|---|---|---|---|---|---|---|---|
| | | A | B | C | D | E | F | G | H | I | J |
| Potassium SE | 2-90 | 15 | 15 | 15 | 15 | 18 | 18 | 18 | 15 | 15 | 18 |
| Sodium SE | combined total | 23 | 23 | 23 | 23 | 28 | 28 | 28 | 23 | 23 | 28 |
| Nonionic surfactant | 2-40 | 18 | 11 | 18 | 11 | 24 | 14 | 14 | 18 | 11 | 14 |
| Alcohol Ether Sulfate | 0-35 | | | | | | | | | | |
| AMMONYX® LO | 0-6 | | | | | | | | | | |
| Oleamide DEA | 0-7 | | 7 | | 7 | | 10 | 10 | | | |
| Coconut fatty acid | 0-10 | | | | | | | | | 7 | 10 |
| Borax pentahydrate | 0-3 | 1.5 | 1.5 | 1.5 | 1.5 | 0.5 | 0.5 | 0.5 | | | |
| Propylene glycol | 0-6 | 1.4 | 1.4 | 1.4 | 1.4 | 1.0 | 1.0 | 1.0 | | | |
| Glycerol | | | | | | | | | | | |
| Sodium citrate | 0-10 | 5.0 | 5.0 | 5.0 | 5.0 | 5.0 | 5.0 | 5.0 | | | |
| Triethanolamine | 0-6 | | | | | | | | 5.0 | 5.0 | 5.0 |
| Monoethanolamine | 0-6 | 4.5 | 4.5 | 4.5 | 4.5 | 4.5 | 4.5 | 4.5 | | | |
| Fluorescent whitening agent (FWA) | 0-1 | 0.2 | 0.2 | 0.2 | 0.2 | 0.2 | 0.2 | 0.2 | 4.5 | 4.5 | 4.5 |
| Antiredeposition agent | 0-1.5 | | | | | | | | 0.2 | 0.2 | 0.2 |
| Thickener | 0-2 | | | | | | | | | | |
| Thinner | 0-20 | 1-3 | | 1-3 | | 3-7 | | | 2-5 | | |

TABLE 7-continued

| Ingredient* | Generic Formula | % Inclusion by Weight (Based on 100% Active) | | | | | | | | | |
|---|---|---|---|---|---|---|---|---|---|---|---|
| | | A | B | C | D | E | F | G | H | I | J |
| Protease | 0-2 | 1.1 | 1.1 | 1.1 | 1.1 | 1.2 | 1.2 | 1.2 | 1-3 | | |
| Amylase | 0-2 | 0.55 | 0.55 | 0.55 | 0.55 | 0.6 | 0.6 | 0.6 | | | |
| Lipase | 0-2 | | | 0.25 | 0.25 | | | | | | |
| Mannanase | 0-2 | | | 0.13 | 0.13 | | | | | | |
| Cellulase | 0-2 | | | 0.02 | 0.02 | | | | | | |

* * A preferred nonionic surfactant is BIO-SOFT ® N25-7, Stepan Company. A preferred alcohol ether sulfate is sodium laureth sulfate, available as STEOL ® CS-460, from Stepan Company, Northfield, IL. A preferred FWA is TINOPAL CBS-X, available from Ciba. A preferred thickener is high molecular weight (e.g. greater than 100,000 daltons) hydroxyethylcellulose, such as Cellosize QP 100MH, available from Dow Chemical. Preferred high molecular weight hydroxyl celluloses include those having a molecular weight of at least about 100,000, alternatively at least about 300,000, alternatively at least about 500,000 daltons. Preferred thinners include: $C_{12}EO_2$, $C_{12}EO_3$, sorbitan monolaurate, propylene glycol, sorbitol, glycerol, ethanol, isopropanol, sodium xylene sulfonate, sodium cumene sulfonate, 2-methoxy ethanol, 2-butoxyethanol, methoxy ethoxy ethanol and combinations of these (if any thinners used in a given formula are already being used in the formula on from another row, the amount used as thinner is in addition to that already included),. A preferred preservative for these formulas is Neolone M-10 from Rohm and Haas used at 75 ppm on a 100% active basis.

Examples 19A-M

Bargain Laundry Detergent Formulations

Example: The following prophetic formulas in Table 8 are intended to cover liquid laundry detergent formulas. Unless more narrowly defined in the table, the pH of these formulas is between about 10 and about 12.5, preferably between about 11.0 and about 12.0 and most preferably between about 11.3 and about 11.8. In each case, these are intended to be liquid detergent formulas and, after the addition of optional ingredients, water would be used to bring the total weight up to 100%. The ingredients are listed on a "100% Active" basis, meaning that the total weight percentage is not diluted but rather 100% of the ingredient.

CONCLUSION

The embodiments and examples described herein are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted.

What is claimed is:

1. A composition comprising a mixture of sodium and potassium salts of sulfo-estolides, which have the following Formula:

TABLE 8

| Ingredient* | Generic Formula | % Inclusion by Weight (Based on 100% Active) | | | | | | | | | | | | |
|---|---|---|---|---|---|---|---|---|---|---|---|---|---|
| | | A | B | C | D | E | F | G | H | I | J | K | L | M |
| Potassium SE | 2-90 | 15 | 15 | 14 | 15 | 14 | 18 | 17 | 18 | 17 | 18 | 18 | 17 | 17 |
| Sodium SE | combined total | 22 | 22 | 21 | 22 | 21 | 27 | 26 | 27 | 26 | 27 | 27 | 26 | 26 |
| Nonionic surfactant | 2-40 | 28 | 28 | 28 | 18 | 18 | 30 | 30 | 17 | 17 | 30 | 17 | 30 | 17 |
| Alkyl Ether Sulfate | 0-35 | | | | | | | | | | | | 2 | 2 |
| AMMONYX ® LO | 0-6 | | | 2 | | 2 | | 2 | | 2 | | 13 | | 13 |
| $C_{12}EO_3$ | 0-13 | | | | 10 | 10 | | | 13 | 13 | | | | |
| Coconut fatty acid | 0-10 | | | | | | | | | | 7 | 7 | 7 | 7 |
| Sodium metasilicate | 0-10 | | | | | | | | | | | | | |
| Sodium carbonate | 0-10 | 8 | 8 | 8 | 8 | 8 | 8 | 8 | 8 | 8 | 0.25 | 0.25 | 0.25 | 0.25 |
| Fluorescent whitening agent (FWA) | 0-1 | 0.25 | 0.25 | 0.25 | 0.25 | 0.25 | 0.25 | 0.25 | 0.25 | 0.25 | | | | |
| Antiredeposition agent | 0-1.5 | | | | | | | | | | | | | |
| Thickener | 0-2 | | | | | | | | | | 5 | | 5 | |
| Thinner | 0-20 | | 3 | 3 | | | 5 | 5 | | | 45 | 45 | 43 | 43 |

*A preferred nonionic surfactant is BIO-SOFT ® N25-7, Stepan Company. A preferred alcohol ether sulfate is sodium laureth sulfate, available as STEOL ® CS-460, Stepan Company. A preferred FWA is TINOPAL CBS-X, Ciba. A preferred thickener is Cellosize QP 100MH, Dow Chemical, Midland, Michigan. Preferred thinners include: $C_{12}EO_2$, $C_{12}EO_3$, sorbitan monolaurate, propylene glycol, sorbitol, glycerol, ethanol, isopropanol, sodium xylene sulfonate, sodium cumene sulfonate, 2-methoxy ethanol, 2-butoxyethanol, methoxy ethoxy ethanol and combinations of these.

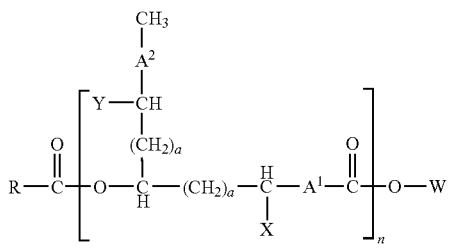

wherein n is an integer from 1-30;
one of X and Y is SO$_3$—Z, the other of X and Y is H, and X and Y are independently assigned in each repeating unit;
A$^1$ and A$^2$ are linear or branched, saturated or unsaturated, substituted or un-substituted, alkyl diradicals wherein the total number of carbons for each repeating unit is independent and in the range of C$_8$ to C$_{22}$;
a is 0, 1, or 2, and is independently assigned in each repeating unit;
R is linear or branched, saturated or unsaturated, substituted or un-substituted hydrocarbon wherein the total number of carbon atoms is from 1 to 24;
W is a sodium or potassium cation, H, or an alkyl or substituted alkyl group; and
Z is a sodium or potassium cation;
wherein the sodium and potassium salts are present in the mixture in amounts sufficient to obtain a composition that is a clear, homogeneous liquid product.

2. The composition of claim 1, wherein the potassium salt is present in the mixture in a weight fraction of about 0.1 to about 0.8 based on the total weight of the potassium and sodium salts in the mixture.

3. The composition of claim 2, wherein the potassium salt is present in the mixture in a weight fraction of about 0.5 to about 0.8 based on the total weight of the potassium and sodium salts in the mixture.

4. The composition of claim 2, wherein the potassium salt is present in the mixture in a weight fraction of about 0.1 to about 0.5 based on the total weight of the potassium and sodium salts in the mixture.

5. The composition of claim 2, wherein the potassium salt is present in the mixture in a weight fraction of about 0.3 to about 0.4 based on the total weight of the potassium and sodium salts in the mixture.

6. The composition of claim 1, wherein the potassium cation is present in the mixture in a molar fraction of about 0.08 to about 0.75 based on the total moles of sodium and potassium cations in the mixture.

7. The composition of claim 6, wherein the potassium cation is present in the mixture in a molar fraction of about 0.43 to about 0.75 based on the total moles of sodium and potassium cations in the mixture.

8. The composition of claim 6, wherein the potassium cation is present in the mixture in a molar fraction of about 0.08 to about 0.43 based on the total moles of sodium and potassium cations in the mixture.

9. The composition of claim 6, wherein the potassium cation is present in the mixture in a molar fraction of about 0.25 to about 0.34 based on the total moles of sodium and potassium cations in the mixture.

10. The composition of claim 1, further comprising about 3% by weight or less of inorganic sulfate.

11. The composition of claim 1, having a pH value of about 6 to about 8.5.

12. The composition of claim 1, wherein the composition is phase-stable, clear and homogeneous for at least 14 days at a temperature of about 22° C.

13. The composition of claim 1 wherein the mixture of sodium and potassium sulfo-estolide salts is present in the composition in a concentration of at least 50% by weight actives.

14. The composition of claim 1, wherein the mixture of sodium and potassium sulfo-estolide salts is present in the composition in a concentration of at least 60% by weight actives.

15. A process for preparing a phase-stable sulfo-estolide composition comprising the steps of:
(a) providing at least one sulfonated intermediate made by sulfonating at least one unsaturated fatty carboxylic acid having 8 to 24 carbon atoms;
(b) reacting the sulfonated intermediate with a chain termination agent having 4 to 24 carbon atoms to form at least one sulfo-estolide;
(c) neutralizing the at least one sulfo-estolide by adding to the at least one sulfo-estolide a caustic agent selected from the group consisting of KOH, NaOH and mixtures thereof to obtain a neutralized sulfo-estolide salt;
(d) bleaching the neutralized sulfo-estolide salt with hydrogen peroxide at a pH level in the range of about 4.5 to about 7.5; and
(e) adding additional KOH, NaOH or mixtures thereof before, during or after the bleaching step in an amount sufficient to obtain a mixture of potassium and sodium sulfo-estolide salts that results in a phase-stable sulfo-estolide composition that is clear and homogeneous.

16. The process of claim 15, wherein the caustic agent for neutralization is KOH, and NaOH or a mixture of NaOH and KOH is added to the sulfo-estolide salt before, during or after the bleaching step to obtain the sulfo-estolide salt mixture.

17. The process of claim 15, wherein the caustic agent for neutralization is NaOH, and KOH or a mixture of KOH and NaOH is added to the sulfo-estolide salt before, during or after the bleaching step to obtain the sulfo-estolide salt mixture.

18. The process of claim 15, wherein the caustic agent for neutralization is a mixture of KOH and NaOH, and NaOH, KOH or a mixture thereof is added to the sulfo-estolide salt before, during or after the bleaching step to obtain the sulfo-estolide salt mixture.

19. The process of claim 15, wherein the bleaching step is carried out at a pH level of greater than about 6.0 to about 7.5.

20. The process of claim 15, wherein the additional KOH, NaOH or mixtures thereof is added in amount sufficient to obtain a pH in the range of greater than about 6.0 to about 8.5.

21. The process of claim 20, wherein the additional KOH, NaOH or mixtures thereof is added in an amount sufficient to obtain a weight fraction of potassium sulfo-estolide salt in the potassium and sodium sulfo-estolide salt mixture of about 0.1 to about 0.8 based on the total weight of potassium and sodium sulfo-estolide salts.

22. The process of claim 20, wherein the additional KOH, NaOH or mixtures thereof is added in an amount sufficient to obtain a weight fraction of potassium sulfo-estolide salt in the potassium and sodium sulfo-estolide salt mixture of about 0.5 to about 0.8, based on the total weight of the potassium and sodium sulfo-estolide salts.

23. The process of claim 20, wherein the additional KOH, NaOH or mixtures thereof is added in an amount sufficient to obtain a weight fraction of potassium sulfo-estolide salt in the potassium and sodium sulfo-estolide salt mixture of about 0.1 to about 0.5, based on the total weight of the potassium and sodium sulfo-estolide salts.

24. The process of claim 20, wherein the additional KOH, NaOH or mixtures thereof is added in an amount sufficient to obtain a weight fraction of potassium sulfo-estolide salt in the potassium and sodium sulfo-estolide salt mixture of about 0.3 to about 0.4, based on the total weight of the potassium and sodium sulfo-estolide salts.

25. The process of claim 20, wherein the additional KOH, NaOH or mixtures thereof is added in an amount sufficient to obtain a molar fraction of potassium cations in the potassium and sodium sulfo-estolide salt mixture of about 0.08 to about 0.75 based on the total moles of potassium and sodium cations.

26. The process of claim 20, wherein the additional KOH, NaOH or mixtures thereof is added in an amount sufficient to obtain a molar fraction of potassium cations in the potassium and sodium sulfo-estolide salt mixture of about 0.43 to about 0.75 based on the total moles of potassium and sodium cations.

27. The process of claim 20, wherein the additional KOH, NaOH or mixtures thereof is added in an amount sufficient to obtain a molar fraction of potassium cations in the potassium and sodium sulfo-estolide salt mixture of about 0.08 to about 0.43 based on the total moles of potassium and sodium cations.

28. The process of claim 20, wherein the additional KOH, NaOH or mixtures thereof is added in an amount sufficient to obtain a molar fraction of potassium cations in the potassium and sodium sulfo-estolide salt mixture of about 0.25 to about 0.34 based on the total moles of potassium and sodium cations.

29. A laundry detergent composition, comprising:
about 2% to about 90% by weight of a mixture of sodium and potassium salts of sulfo-estolides having the following Formula 1:

$$1. \quad R-\overset{O}{\underset{\|}{C}}-\left[O-\underset{H}{\overset{(CH_2)_a}{\underset{|}{\overset{|}{C}}}}-(CH_2)_a-\underset{X}{\overset{H}{\underset{|}{C}}}-A^1-\overset{O}{\underset{\|}{C}}-O\right]_n-W$$

Formula 1 wherein n is an integer from 1-30;
one of X and Y is SO3-Z, the other of X and Y is H, and X and Y are independently assigned in each repeating unit;
A1 and A2 are linear or branched, saturated or unsaturated, substituted or unsubstituted alkyl diradicals wherein the total number of carbons for each repeating unit is independent and in the range of $C_8$ to $C_{22}$;
a is 0, 1, or 2, and is independently assigned in each repeating unit;
R is a linear or branched, saturated or unsaturated, substituted or unsubstituted alkyl radical with from 1 to 24 carbon atoms;
W is a sodium or potassium cation, H, or an alkyl or substituted alkyl group;
Z is a sodium or potassium cation;
about 2% to about 40% by weight of at least one nonionic surfactant;
0% to about 35% by weight of at least one alcohol ether sulfate;
0% to about 6% by weight of lauryl dimethlyamine oxide;
0% to about 10% by weight of oleamide diethanolamine;
0% to about 6% by weight of $C_{12}EO_3$;
0% to about 10% by weight of coconut fatty acid;
0% to about 3% by weight of borax pentahydrate;
0% to about 6% by weight of propylene glycol;
0% to about 10% by weight of sodium citrate;
0% to about 6% by weight of triethanolamine;
0% to about 6% by weight of monoethanolamine;
0% to about 1% by weight of at least one fluorescent whitening agent;
0% to about 1.5% by weight of at least one anti-redeposition agent;
0% to about 2% by weight of at least one thickener;
0% to about 20% by weight of at least one thinner;
0% to about 2% by weight of at least one protease;
0% to about 2% by weight of at least one amylase; and
0% to about 2% by weight of at least one cellulase.

30. The laundry detergent composition of claim 29, wherein the mixture of sodium and potassium salts of sulfo-estolides is present in the composition in an amount of about 15% to about 46% by weight of the composition.

31. The laundry detergent composition of claim 30 wherein the mixture of sodium and potassium salts of sulfo-estolides provides better cleaning of grass stains on cotton than a similar detergent composition containing only a potassium sulfo-estolide salt or only a sodium sulfo-estolide salt in place of the mixture of sodium and potassium salts.

32. A laundry detergent composition, comprising:
about 2% to about 90% by weight of a mixture of sodium and potassium salts of sulfo-estolides having the following Formula 1:

$$R-\overset{O}{\underset{\|}{C}}-\left[O-\underset{H}{\overset{(CH_2)_a}{\underset{|}{\overset{|}{C}}}}-(CH_2)_a-\underset{X}{\overset{H}{\underset{|}{C}}}-A^1-\overset{O}{\underset{\|}{C}}-O\right]_n-W$$

wherein n is an integer from 1-30;
one of X and Y is SO3-Z, the other of X and Y is H, and X and Y are independently assigned in each repeating unit;
A1 and A2 are linear or branched, saturated or unsaturated, substituted or unsubstituted alkyl diradicals wherein the total number of carbons for each repeating unit is independent and in the range of $C_8$ to $C_{22}$;
a is 0, 1, or 2, and is independently assigned in each repeating unit;
R is a linear or branched, saturated or unsaturated, substituted or unsubstituted alkyl radical with from 1 to 24 carbon atoms;
W is a sodium or potassium cation, H, or an alkyl or substituted alkyl group;
Z is a sodium or potassium cation;
about 2% to about 40% by weight of at least one nonionic surfactant;

0% to about 35% by weight of at least one or more alcohol ether sulfate;
0% to about 6% by weight of lauryl dimethlyamine oxide;
0% to about 13% by weight of $C_{12}EO_3$;
0% to about 10% by weight of coconut fatty acid;
0% to about 10% by weight of sodium metasilicate;
0% to about 10% by weight of sodium carbonate;
0% to about 1% by weight of at least one fluorescent whitening agent;
0% to about 1.5% by weight of at least one anti-redeposition agent;
0% to about 2% by weight of at least one thickener; and
0% to about 20% by weight of at least one thinner.

33. The laundry detergent composition of claim 32, wherein the mixture of sodium and potassium salts of sulfo-estolides is present in the composition in an amount of about 15% to about 60% by weight of the composition.

34. A composition comprising a mixture of salts of sulfo-estolides, which have the following Formula:

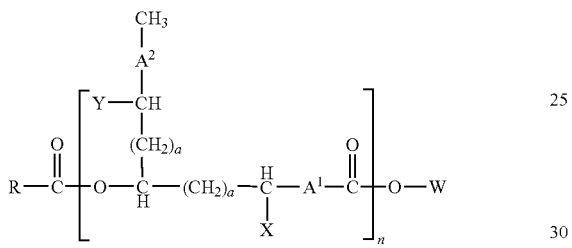

wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or un-substituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or un-substituted hydrocarbon wherein the total number of carbon atoms is from 1 to 24;

W is a cation, H, or an alkyl or substituted alkyl group; and Z is a cation;

wherein the salts are present in the mixture in amounts sufficient to obtain a composition that is a clear, homogeneous liquid product.

* * * * *